United States Patent
Regmi et al.

(10) Patent No.: US 11,989,780 B2
(45) Date of Patent: May 21, 2024

(54) BUSINESS METHOD, APPARATUS AND SYSTEM FOR MANAGING DATA, ANALYTICS AND ASSOCIATED FINANCIAL TRANSACTIONS FOR ENVIRONMENTAL, ENGINEERED AND NATURAL SYSTEMS

(71) Applicant: Resilience Financing Inc., Middletown, DE (US)

(72) Inventors: Pusker Regmi, Rockville, MD (US); Daniel Medina, Silver Spring, MD (US); Kieran Iyengar, Herndon, VA (US); Sudhir Murthy, Herndon, VA (US); James Clarke, Washington, DC (US)

(73) Assignee: WaterwAIs Inc., Herndon, VA (US)

( * ) Notice: Subject to any disclaimer, the term of this patent is extended or adjusted under 35 U.S.C. 154(b) by 0 days.

(21) Appl. No.: 16/912,667

(22) Filed: Jun. 25, 2020

(65) Prior Publication Data

US 2020/0410590 A1    Dec. 31, 2020

Related U.S. Application Data

(60) Provisional application No. 62/866,590, filed on Jun. 25, 2019.

(51) Int. Cl.
*G06Q 40/04*       (2012.01)
*B64C 39/02*       (2023.01)
(Continued)

(52) U.S. Cl.
CPC ........... *G06Q 40/04* (2013.01); *B64C 39/024* (2013.01); *G01N 33/0004* (2013.01);
(Continued)

(58) Field of Classification Search
CPC ........ G06Q 40/02; G06Q 40/04; G06Q 40/08; G06Q 40/10; G06Q 40/12; G06Q 10/10;
(Continued)

(56) References Cited

U.S. PATENT DOCUMENTS 8,046,295 B1 * 10/2011 Cohan ............... G06Q 40/04
                                                    705/37
8,280,633 B1 * 10/2012 Eldering .............. G06Q 40/08
                                                    702/3

(Continued)

OTHER PUBLICATIONS

Gugnani et al., "Analysis of deep learning approaches for air pollution prediction", Multimedia Tools and Applications (2022) 81: 6031-6049, Nov. 5 . (Year: 2021).*

(Continued)

*Primary Examiner* — Frantzy Poinvil
(74) *Attorney, Agent, or Firm* — Leverage Law Firm LLC; James Lowell Ramsey Clarke

(57) ABSTRACT

The subject of the invention is an insurance claim and/or financial transaction processing system for parametric risk related claims and/or performance warranty related transactions that can be processed using transparency and in a rapid manner wherein the performance or insurance is transacted using sensors and/or analytics. The invention also includes a marketplace where parties can enter or leave, buy or sell, a transaction or transactions associated with an insurance or financial transaction. The system enables aggregation and/or distribution of risk, performance obligations or investments, and aggregation/distribution and/or syndication of insurers or bankers, crowdsourcing/crowdfunding and/or participation of individuals and small groups within the transaction system. The integration of investment, insurance risk conditionalities and performance guarantees within a single (Continued)

exchangeable system is also envisioned. Transaction re-risking and de-risking and associated payments or payouts is also envisioned.

8 Claims, 10 Drawing Sheets

(51) Int. Cl.
| | |
|---|---|
| G01N 33/00 | (2006.01) |
| G01N 33/18 | (2006.01) |
| G01N 33/24 | (2006.01) |
| G01N 33/38 | (2006.01) |
| G06F 16/23 | (2019.01) |
| G06Q 10/0635 | (2023.01) |
| G06Q 10/10 | (2023.01) |
| G06Q 20/08 | (2012.01) |
| G06Q 20/36 | (2012.01) |
| G06Q 30/012 | (2023.01) |
| G06Q 30/018 | (2023.01) |
| G06Q 30/0282 | (2023.01) |
| G06Q 40/02 | (2023.01) |
| G06Q 40/08 | (2012.01) |
| G06Q 40/10 | (2023.01) |
| G06Q 40/12 | (2023.01) |
| G06Q 50/02 | (2012.01) |
| G06Q 50/06 | (2012.01) |
| G06Q 50/16 | (2012.01) |
| G06Q 50/26 | (2012.01) |
| H04L 69/324 | (2022.01) |
| B64U 101/00 | (2023.01) |

(52) U.S. Cl.
CPC .............. *G01N 33/18* (2013.01); *G01N 33/24* (2013.01); *G01N 33/383* (2013.01); *G06F 16/2379* (2019.01); *G06Q 10/0635* (2013.01); *G06Q 10/10* (2013.01); *G06Q 20/085* (2013.01); *G06Q 20/3678* (2013.01); *G06Q 30/012* (2013.01); *G06Q 30/018* (2013.01); *G06Q 30/0282* (2013.01); *G06Q 40/02* (2013.01); *G06Q 40/08* (2013.01); *G06Q 40/10* (2013.01); *G06Q 40/12* (2013.12); *G06Q 50/02* (2013.01); *G06Q 50/06* (2013.01); *G06Q 50/16* (2013.01); *G06Q 50/26* (2013.01); *H04L 69/324* (2013.01); *B64U 2101/00* (2023.01)

(58) Field of Classification Search
CPC .............. G06Q 10/0635; G06Q 20/085; G06Q 30/012; G06Q 30/018; G06Q 30/0282; G06Q 50/02; G06Q 50/06; G06Q 50/16; G06Q 50/26; G06F 16/2379
USPC ...................................................... 705/3–44
See application file for complete search history.

(56) References Cited

U.S. PATENT DOCUMENTS

| | | | | |
|---|---|---|---|---|
| 8,306,892 | B1* | 11/2012 | Gross ..................... | G06Q 40/06 705/36 R |
| 9,947,051 | B1* | 4/2018 | Allen ..................... | G06Q 50/16 |
| 10,161,749 | B1* | 12/2018 | Wu ......................... | G06F 30/18 |
| 10,856,116 | B1* | 12/2020 | Klein ..................... | H04W 4/021 |
| 11,549,837 | B2* | 1/2023 | Klicpera ............... | G06Q 50/06 |
| 11,556,997 | B1* | 1/2023 | Corder ................... | G06Q 40/08 |
| 2002/0069149 | A1* | 6/2002 | Maxwell ............... | G06Q 40/02 705/36 R |
| 2007/0083457 | A1* | 4/2007 | Evelyn ................... | G06Q 40/04 705/37 |
| 2009/0187504 | A1* | 7/2009 | Monaco ................ | G06Q 40/04 705/37 |
| 2016/0284029 | A1* | 9/2016 | Rhodes .................. | G06Q 40/08 |
| 2019/0271578 | A1* | 9/2019 | Moeller ................. | G06Q 10/083 |
| 2019/0304025 | A1* | 10/2019 | Szott ...................... | G06Q 40/08 |
| 2019/0311443 | A1* | 10/2019 | Blades ................... | H04L 9/3239 |
| 2020/0143300 | A1* | 5/2020 | Weldemariam ..... | G06F 16/1805 |
| 2021/0263909 | A1* | 8/2021 | Paracha ............. | G06Q 10/0639 |

OTHER PUBLICATIONS

Krishnan et al., "Smart water Resource management using Artificial Intelligence_A Review", DOI : http://dx.doi.org/10.3390/su142013384, Oct. 17 (Year: 2022).*

* cited by examiner

600

Restoration and Resiliency

| Parameter | Factor or Weight | Value (tokens) |
|---|---|---|
| Flow (Q) | ± $\omega_Q$ | $\omega_Q \times Q$ |
| Sediment (S) | ± $\omega_S$ | $\omega_S \times S$ |
| Bacteria (B) | ± $\omega_B$ | $\omega_B \times B$ |
| Carbon (C) | ± $\omega_C$ | $\omega_C \times C$ |
| Nitrogen (N) | ± $\omega_N$ | $\omega_N \times N$ |
| Phosphorus (P) | ± $\omega_P$ | $\omega_P \times P$ |
| Trash (T) | ± $\omega_T$ | $\omega_T \times T$ |
| Micropollutants (M) | ± $\omega_M$ | $\omega_M \times M$ |

Water Quality Types

| Pollutant | Factor or Weight (tokens/pollutant) | Pollutant Value (tokens) |
|---|---|---|
| Chlorophyll (L) | ± $\omega_L$ | $\omega_L \times L$ |
| Toxicity (X) | ± $\omega_X$ | $\omega_X \times X$ |
| Turbidity (S) | ± $\omega_S$ | $\omega_S \times S$ |
| Microbiology (M) | ± $\omega_M$ | $\omega_M \times M$ |
| Aesthetics (T) | ± $\omega_T$ | $\omega_T \times T$ |

FIG. 6

BUSINESS METHOD, APPARATUS AND SYSTEM FOR MANAGING DATA, ANALYTICS AND ASSOCIATED FINANCIAL TRANSACTIONS FOR ENVIRONMENTAL, ENGINEERED AND NATURAL SYSTEMS

CROSS-REFERENCE TO RELATED APPLICATIONS

The present application claims priority to U.S. Provisional Patent Application No. 62/866,590, filed Jun. 25, 2019. The entire disclosure of U.S. Provisional Patent Application No. 62/866,590 is incorporated herein by reference.

BACKGROUND

Connecting financial transaction with parametric and performance related data and analysis in an environmental and energy system can be leveraged into everyday contracts.

Financial transactions predicated upon conditions or contingencies are common and are becoming more prevalent as a means to mitigate risk or to assure performance or to develop alternate future returns for cash flow from a mitigated risk, hazard or pollution. In some cases, a combination of these approaches is possible. There is a need for a more transparent digital platform where such transactions can be monitored in a transparent manner and where the data is secure and validated.

A private marketplace where such transactions are bought and sold in the form of insurance or insurance bonds, including but not limited to financial bonds, municipal bonds, catastrophe bonds, resilience bonds, restoration bonds, or hybrid annuities can also exist where typically a syndicate of investors or a syndicate of insurers may invest or insure in a performance driven project or a parametric insurance that considers an event risk. A transparent public marketplace where a syndicate can be created to invest in such projects related to parametric insurance or project performance can also be envisioned. Furthermore, the ability to buy and sell or bundle warranties, sureties and insurance is also needed. This can occur in the form of an exchange that can contain transactions related to likelihood of occurrence of events or the likelihood of performance of a project that for example mitigates events or mitigates air, water or soil pollution.

The subject of the invention is the development of methods, apparatus and systems to manage an environment, energy or nature=based infrastructure transaction, an exchange or to develop a marketplace for such transactions or an exchange.

SUMMARY

The subject of the present disclosure is the development of a blockchain or otherwise other options of immutable, transparent and/or an instantly or near instantly (or realtime) retrievable financial transaction management system to facilitate the evaluation and/or resulting payout and/or assessment of fixed or variable premium or coupon or other forms of credit or debt-transactions associated with an event or performance or warranty or parameter in an environmental or energy or nature-based event or performance of associated infrastructure or insurance or warranty management system.

A centralized approach could also be used for such transactions along with third parties that are used for verifying and/or authenticating transactions or records. Henceforth, any mention of blockchain could be replaced or interchanged with centralized platform approaches or vice versa or other approaches along the centralized-decentralized cline, that provide equivalent or near equivalent capabilities for addressing the intent (a project(s) or trust(s) or Special Purpose Vehicle(s) (SPV)(s)) to address an environmental or energy or nature-based engineered infrastructure or natural systems (such as wetlands) transaction event). In some cases, immutability may not be essential and such features can be ignored in a particular application. A combination of a blockchain and centralized approach can also be envisioned in a modular manner, for example if privacy needs to be protected, or to speed up particular transactions, or to reduce computing resources needed, or to provide immutable approaches only where and when needed. Such chunking and modularization have been envisioned in this invention.

This system can be used to manage transactions and/or environments including but not limited to a single transaction, multiple transactions, an exchange, or a marketplace, watersheds, airsheds or energysheds (defined as the raw inventory of available energy such as from carbon, nuclear, hydro, solar and/or wind) and the corresponding capture, control, cleanup, adaptation or mitigation for a single or multiple purpose. The parties involved could be (and not limited to) individuals, high net worth individuals, sponsor or sponsors, insurers, syndicate of insurers, investor, syndicate of investors, issuer or issuers, builder or builders, contractor or contractors, farmers, residents, dischargers or polluters, governmental and non-governmental agencies, authority or authorities, public-private partnerships, businesses, developers, regulators or other third parties.

The exchange, marketplace or platform could be facilitated through a special purpose vehicle, special purpose entity, special purpose company or special purpose authority. These special purpose terms can be interchangeably used. The purpose of such authority/entity/vehicle/company is to address specific goals that could be short term, long term and in some cases permanently in place. This vehicle allows for pooling of parties or also allows for 'ring-fencing' or conversion of risk, equity, bonds, and/or other types of fiat or crypto currencies or cash-flow obligations. These vehicles/entities or the exchange could have a legal charter that can be composed or programmed into a or smart law/bylaw (such as where the voting is automated to allow various features of a bill), and/or smart regulation (such as where an enabling regulation is promulgated or modified based on for example a voting approach of a committee or a board) and/or smart contract and/or smart agreement. All of these laws regulations and agreements collectively fall under the broad category of smart contract regardless of the it being a law, regulation or agreement.

This system can contain a computing system or a supercomputing system that can monitor, analyze and/or predict simple or very complex events or performance and their likelihood in order to provide transparency and/or early warning or prediction or prognostics associated with likelihood of a payout associated with a trigger.

The transaction associated with the event or performance is determined by a static or a dynamic (changing) contract or smart contract, where the algorithm associated with the contract triggers the transaction and trust associated with the transaction, this algorithm can be simple or layered or nested in a way that the payouts or transactions could occur in installments associated with a single event or performance, or multiple events and performance over multiple space or time thresholds.

The trigger could be a conditional or a contingent payment that could be a single payment or a series of payments that are optionally time based or event occurrence based or to optionally facilitate cashflow such as in the form of an annuity or reverse annuity.

All data and analytics are stored, and all information is retrievable through a historian that records all data and changes made to the data. This data could be information that is associated with manual or automated sensing or from manual or automated analysis. The data can have reliability and probabilistic confidence values, or signatures or hierarchies based on sensor quality or data quality or event or performance priority. Such sensors can be fixed, or mounted, on a satellite or in a drone or a buoy or a water vehicle.

Payouts can be triggered as a single value or a range of payment values for a single event or multiple events or for a single performance or multiple performance attainment. A payout can also be a range based on probabilistic confidence of a likelihood of event occurrence or likelihood of performance achievement.

The transaction could, as an example, be an insurance (such as a parametric insurance) or a warranty (such as a performance guarantee). The cash or cashflow that is raised could be associated with a bond, stock, annuity, reverse annuity, a fund or any financial instrument. Other approaches are also possible.

BRIEF DESCRIPTION OF THE SEVERAL VIEWS OF THE DRAWINGS

The accompanying drawings which are incorporated in and form a part of the specification, illustrate several embodiments of the invention wherein:

FIG. 6 is an overview drawing providing an example of tokenization based on restoration and resiliency parameters as well as water quality indicators.

DETAILED DESCRIPTION

Figure 1:
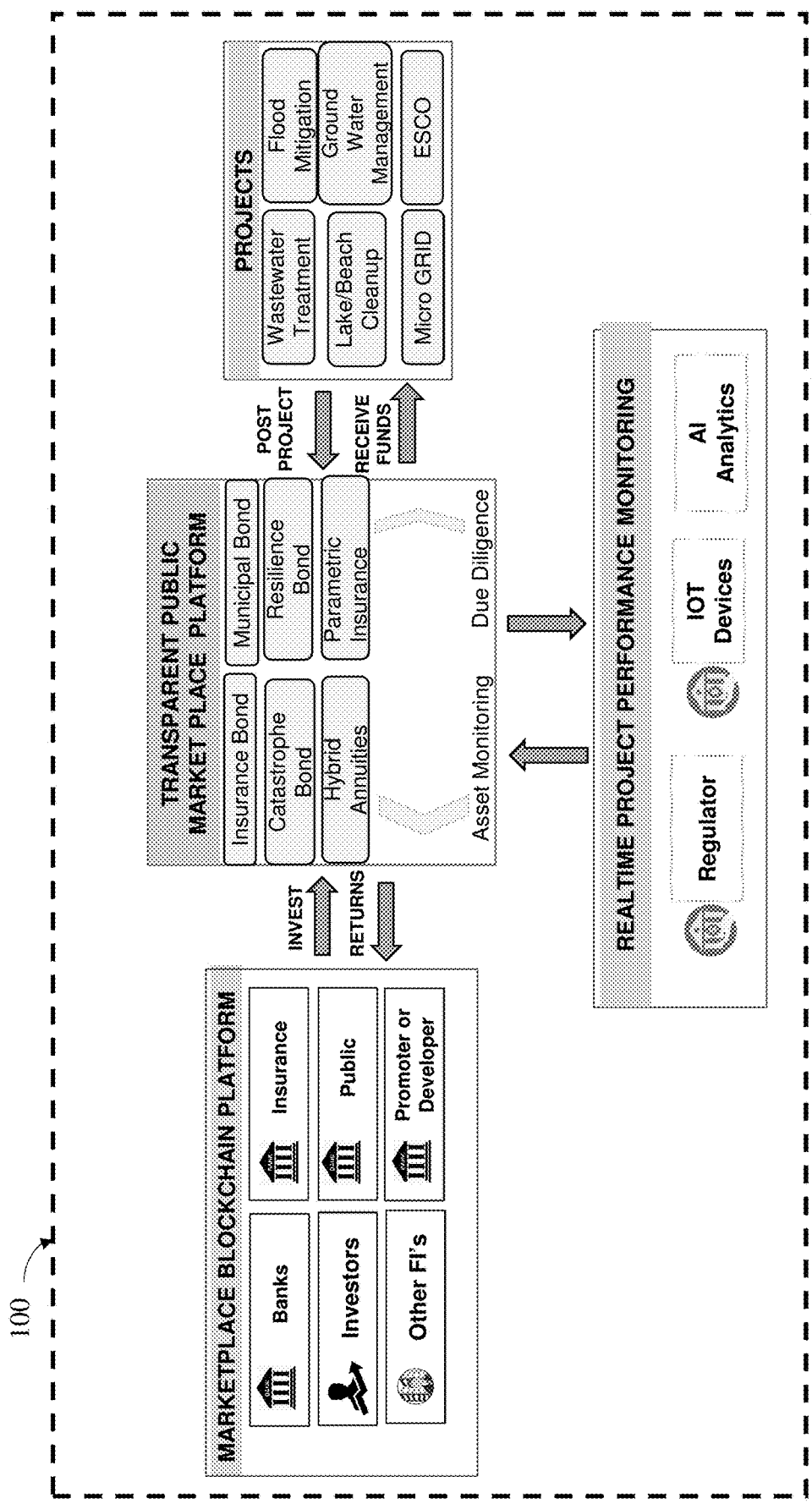
FIG. 1 is an overview drawing showing an exemplary system, method, and apparatus (a computerized platform) that can be used to develop transactions that are contractual.

Environmental and Energy systems are subject to vagaries of performance or subject to disasters. For example, the ability of a power grid to supply energy reliably is a performance based or warranty-based risk, forest fires are sometimes caused by these same grids and such grids can become a disaster risk. Water quantity and quality management can be an acute event hazard (such as a flood or a pollutant spill) as well as a performance or warranty metric (such as a levee that protects against a flood or the performance of a wastewater treatment plant). Air pollution management and disasters from high winds are also subject to performance and risk. Pollution can occur from disperse sources or a point source, and the event or performance can be held by a group (such as farmers or residents) or a single party (industry).

The invention proposes to optionally combine the investments and insurance associated with an energy or environmental system with a transparent, optionally immutable or automated blockchain or blockchain type system to collect data/analytics and to allow such a system to be accessed in a distributed manner by many investors, many sponsors and/or multiple issuers of such transaction. This system would drive down transaction costs and increase trust while making financing and insurance more accessible. This invention can also distribute performance and warranty obligations to more dispersed parties engaged in activities such as farming, home owning, commerce or industry (such as a group of tanneries or electroplaters). The achievement of a performance obligation can incentivize a payout, and a non-achievement could result in a fee, fine or a tax. The achievement of an insurance obligation can result in a payout if a parameter or a set of parameters are satisfied. The method, apparatus or system that is envisioned could handle all such issues, approaches or transactions.

Yet another exemplary embodiment of the present disclosure is a business method comprising: allotting one or more financial instruments and the performance associated with these financial instruments is determined using a transparent blockchain platform at predetermined set points as triggered by one or more respective real world events, said real world events being either a disaster triggered where a payout is triggered on the blockchain, the achievement of a predetermined goal by the party allotted to also triggered on the blockchain where multiple parties participate on the blockchain, or the occurrence of an event that causes losses to the party allotted to or by or would cause loss to the party allotted by but for the establishment of a mitigation project created by the party allotted to and funded by said financial instrument. The triggers for these events are also pre-defined and made transparent on a blockchain where data is immutable and transparent.

Environmental pollution and hazards are increasingly common today, in a perfect storm, as the world population increases, world GDP increases, and climate change effects magnify. Environmental factors can be broadly divided into 'quantity' and 'quality' issues. Storm flows, floods and hurricane can produce huge amount of damage and contingencies are increasingly required to manage these events. An environmental disaster (flood, wind, earthquake, fire, etc.) insurance can protect a sponsor or beneficiary from a loss associated with that event. Such insurance can be parameterized and have payment triggers based on occurrence as well as severity of occurrence. The method, apparatus or system that is envisioned could handle all such issues, approaches or transactions.

The performance or warranty associated with a lamination lagoon, levee or dam used to protect against disaster (such as flood) can also be insured or subject to engineering standards, bonding requirements, and/or performance guarantees or bank guarantees. Finally, a disaster mitigation project can address/mitigate future damage to homes in 'flood plains', thus increasing property values and produce considerable wealth and tax revenues associated with such wealth. The increase in future wealth can also be part of a contingent or conditionality or through tax increment financing, betterment tax or a real estate special purpose vehicle. A tax-like approach can also be instituted where the increment increase is managed internal to a special purpose vehicle to improve trust associated with the wise use of funds and eliminate the middleman. The environmental disaster mitigation could be associated with a structure built to withstand an earthquake, a fire wall to prevent a forest fire, structures built to withstand high winds or any such project that can carry a warranty or an obligation. Other green infrastructure that is decentralized is also feasible. These could include examples of water storage units (rain barrels), rain gardens, porous pavements, green roofs, etc. in private or public space. This warranty could be held by a single party or by multiple parties, such as payout based on severity of an event occurrence and/or severity of failure of a mitigation project. The warranty could also be held by a community or a cooperative. These warranties could be passed on to financial institutions with premiums associated with an entity holding such warranties. The method, apparatus or system that is envisioned could handle all such issues, approaches or transactions.

Environmental pollution of water, air and soil are also subject to conditionality. The pollution of a lake, river or soil by a break in a levee holding or pipe transporting hazardous material is usually insured against such losses. The performance of such levees can also be subject to insurance or warranties. Treatment of pollution or the pollutants and the performance of such treatment processes can be subject to conditionalities. The increase in wealth and tax increments associated with industrial activities (that cause pollution) and its clean up can also be subject to future conditionalities. The polluter could be an individual, such as owner of a failed septic tank, or a farmer that uses too much fertilizer or that burns croplands, an industry such as a small tannery or large pharma, or a utility entrusted with managing sewage. The opportunity is for a polluter to become a sponsor or even an investor, where an issuer of a bond or an instrument or a token, develops financial or insurance approaches to any harm caused by pollution and then develops performance conditionalities or warranties for mitigating such pollution. These conditionalities can reduce premiums for pollution or otherwise create incentive conditionalities for addressing pollution. If such desirable performance generates financial benefits for a community (improved health, property values or tourism), such benefits can be looped back in a 'payment for performance' approach. Other pollution prevention approaches are also possible, where 'scarcity' can be engineered with less pollutant being produced in the first place, or conversely 'abundance' can be conceptualized for gradually worsening climatic events. Such scarcity or abundance associated with an event and/or the addressing of such scarcity or abundance can be tokenized. In one more example, it can take more work and expense to remove the last pollutant compared to the first pollutant, thus the expense for such mining results in same tokenized rewards but the cost to attain these tokens can change with time, such that early cleanup efforts can result in more pollutant removal with less work and fiat expense to attain the token. A logging system containing a historian can allow for summing of such events (and associated flow, load or pollution) to allow for triggers and resulting payments to be distributed over an extended time period.

A project or a watershed restoration or management or an event mitigation (resilience) approach could be part of a special purpose vehicle. The special purpose vehicle (SPV) associated with the adaptation, mitigation or restoration could be unified or linked or connected to other SPVs, such as with a real estate SPV. Thus, an increase in real estate valuations associated with the SPV could then optionally improve valuations of tokens or increase the number of tokens linked to environmental improvements that could have caused such improved valuations. Other linked SPVs are also possible thus directly connecting development (such as tourism improvements, property value increase, health improvements, insurance premium reductions, etc.) to restoration, resilience or environmental improvement. The method, apparatus or system that is envisioned could handle all such issues, events or transactions.

In the European Union, the Polluter Pays Principle is for example used to manage pollutant loads such as nitrogen, phosphorus and chemical oxygen demand to a river or other types of water bodies. This payment is made typically to a regulatory entity or city, in the form of a fixed Euros/kg of load or flow discharged to a water body. While this approach is not a pollution insurance, it serves a similar purpose where a polluter pays a fee to discharge and is incentivized to perform by discharging less pollution. The fee can be integrated into a warranty approach or an insurance approach and its value could be fixed, variable or floating based on performance or improvements in performance of a watershed or airshed with a future conditional triggered payout associated with its prevention. A marketplace exchange could make such payments variable based on real harm caused or real benefits realized. A blockchain or blockchain type (or otherwise a centralized or SPV type) marketplace can be developed where for example a benefit such as future wealth in improved property values can pay for mitigating todays' or past pollution, and/or otherwise, current polluter premiums or discharge payments can do so likewise. The method, apparatus or system that is envisioned could handle all such transactions. The terms blockchain and ledger are used interchangeably. The terms performance, warranty and guarantee are used interchangeably. The terms parametric insurance and disaster bonds can be replaced (or interchanged) with each other even though their use as instruments may differ somewhat in implementation.

Risk or Performance Prioritization and/or Collectivization: A blockchain or centralized approach containing parametric risk or performance obligations can be tied to many micro risks and micro performance that can be collectivized into a macro risk or performance approach. Three examples are provided in the next two paragraphs, one for the energy sector and second and third for the water sector. Other examples of such performance and risk collectivization and/or prioritization such as within a smart contract are also possible and are well within the scope of this invention.

Many facilities, both industrial and/or municipal are developing new approaches for mitigating climate change by reducing their carbon or energy footprint with performance or warranty expectations. Same applies to residences or blocks of residences that choose to generate and/or use power. Same applies to power generation station that generate power. Same applies to battery stations and or reservoirs that hold a head of water (use energy to raise water when prices are cheap and to run turbines when prices are expensive) based on performance expectations. This management and associated performance of energy or carbon or electrons 'net' use or 'net' production of a process, technology or facility can be managed within a grid or a microgrid. The overall approach of many microgrid performance can be assessed by linking them all up through a blockchain or centralized smart contract with performance related warranties assigned to each node and/or grid. These nodes or grids can also be prioritized or weighted in terms of relative importance to develop algorithms and analytics for required performance for energy generation or use with any time period or time constants—instantaneous, minute, hour, day, month, season, year or decade. In the above case, net is defined as the mod of difference of generation and consumption.

Similarly water conservation and water leakage performance warranties can be assigned within a water grid, and these performances can be evaluated transparently on a blockchain or using a more centralized approach, optionally to include underlying parametric risk (such as from and not limiting to a freezing or pressure transient episode leading to a pipe burst) and/or performance warranties (managing leaks). The performance of each node, grid, DMA or virtual DMA can be assessed using a blockchain or other digital approaches.

The pollution insurance or performance of a system can be as large as a river basin, such as the Ganges River or Mississippi River, or a large watershed, airshed or soil system that can be broken up and/or distributed into smaller scale pollution (such as lakes and reservoirs) or performance or warranty obligations of say of municipal, agriculture, or industrial discharges or mitigations, respectively. The meeting of the individual parts can be aggregated into an overall whole in an overall blockchain or a performance and/or insurance ledger. There could also be multiple pollutants (such as carbon, nitrogen, phosphorus, micropollutant, microorganisms, trash, sediment) and multiple improvement indicators (such as turbidity, chlorophyll, microbiological, aesthetic). A weight (associated with its relative importance, resulting benefit, or resulting harm caused) can be assigned to a pollutant or its improvement or its end benefit to the community (in the short- or long-term) to allow for aggregation or trading within a smart contract or a performance warranty.

Example of a centralized non-tokenized approach for an environmental pollution restoration transaction: In a non-tokenized approach, there is a set of minimum targets that must be achieved to arrive at a goal, for example, established minimum amounts of various pollutants that must be removed annually with the goal to restore the health of a lake or a river, as determined through a scientifically defensible study or model. The importance of each target can be expressed through numerical weights that indicate the importance towards achieving the goal. The targets can be achieved individually or as a combination and investors can chose how to contribute towards the main goal.

Usually there are several technological options associated with each target. These technologies offer various intrinsic performance features, for example, efficiency and unit cost to achieve the target. There are also extrinsic features that affect the applicability of given technologies. These extrinsic features are usually constraints imposed by site-specific circumstances surrounding the investment. For instance, in the example above, there may not be land readily available to implement certain pollutant removal technologies. Some technologies depend on others and must be deployed sequentially, for example, a wastewater treatment plant needs a collection system that takes the wastewater to the plant. This type of constraint is also an intrinsic feature.

The combination of weights and intrinsic and extrinsic features defines the initial investment landscape and the platform uses it to determine the return on the investment. Thus, high-performing and fast-performing technologies receive greater returns. However, as the investments accrue credits, it will become more difficult to achieve incremental progress towards meeting the goal; therefore, the platform will adjust the repayment terms will dynamically to assign better returns and encourage investments that were less attractive initially.

Most technologies experience performance degradation with time and require some type of maintenance to preserve that performance. Some investments, particularly in the category of nature-based-solutions, improve their performance with time as they mature, for example, wetlands for water quality improvement and mangroves for protection against hurricanes. In either case, the repayment is contingent upon long-term performance.

Payment to investors is processed through smart contracts. Once a claim for performance is placed, subsequent verification triggers an automated payment and updates the investment landscape to reflect the portion of the goal that was achieved. This update implies retiring options no longer available and enabling others that became possible due previous accomplishments. Verification of the claims is automated in the platform based on performance data collected through sensors and from manual data gathering later uploaded to the platform. Performance metrics depend on the type of technology. In closed systems where it is possible to measure inputs and outputs, the metrics are more reliable than in open systems in which it is not possible to account for all the inputs and outputs. An example of the former is a treatment plant, whose performance can be routinely measured by sampling the effluent from the plant outfalls prior to discharge to a water body. An example of the latter is riparian buffers along a stream, in which it is difficult to account for all the water and pollutants entering and leaving the buffer. In the case of open systems, the platform performs mathematical modeling to estimate the performance metrics. Because modeling introduces uncertainties, its estimates of performance are less reliable than those from actual data collected. Therefore, as a factor of safety, the platform assigns higher targets to more uncertain technologies.

The platform maintains a dashboard that reports progress and performance in real time—or nearly so if manual data are needed. Investors can view options available as well as the anticipated repayments. The platform also publishes historical data on the performance and reliability of all technologies applied, which fosters competition and innovation.

The insurance or performance obligations can be chronic/cumulative or acute/episodic event risk or performance. The insurance or performance obligations can be related to pollution concentration (quality) or mass/volume (quantity) or some other metric (such as a Richter scale for earthquakes or concentrations).

The source of cashflow from pollution fees can serve as base payments or positive incentives or negative incentives (disincentives) in an overall transparent system involving individuals and entities, everyone doing their bit for the environment. A key to managing this marketplace and the disbursement of funds or risk premiums or performance premiums is the use of a transparent and immutable approach for managing data, its analysis and any disbursements and payouts. Sensors (both static or mobile or also satellite) are used to determine risk or performance, and/or modeling approaches used to provide forecasting, uncertainty analysis and predictions. The method, apparatus or system that is envisioned could handle all such issues and transactions.

A key to developing transactions are sound and reliable measurements that can be recorded real-time or near real-time into an immutable and instantly retrievable system. Increasing transparency will also bring more and new parties to a marketplace or exchange and create a more distributed approach for managing performance, warranty and for addressing event or performance risk while at the same time assuring cash-flow and/or investments and the fixed, variable or floating premiums or coupons associated with those transactions. Sensor and data validation methods have also become more sophisticated as the management of 'big data' becomes a common part of our lifestyle. The reliability of making analyses with such data can now become a fundamental part of many transactions. The accuracy and likelihood of the predictions can also be determined and used with probabilistic estimates and/or confidence intervals. The method, apparatus or system that is envisioned could handle all such issues, events or transactions.

Buying or Selling Insurance, warranties/performance guarantees/bonding that helps build infrastructure to avert a disaster can be actively bought or sold in the blockchain or blockchain type marketplace associated with an event. Primary bond holder (say $\frac{1}{10}^{th}$ of bond value) can subrogate the insurance or financial transaction to other players also on this system.

Data confidence and probability. The confidence in data can be estimated using analytics. The approach to evaluate confidence intervals, probability and statistical validity of data and associated analytics can be included within smart contracts to provide a data quality probabilistic parameter associated with a trigger. Payouts can vary based on data quality or a probability associated with a trigger being met. These payouts can be pro-rated or defined in other linear or non-linear, logarithmic or exponential approaches. Validation models can be included to ensure that the data is qualified before payments are triggered. The identity, validity and quality of the devices can be tagged and ascertained in a unique manner or with unique identifiers. The change in quality or validity can also be recorded. A payout trigger can also be qualified based on the quality of the sensor and/or data. For example, a needed human intervention can be taken into consideration within a data quality parameter and the resulting payout. This allows for a payout trigger range or else a trigger based on data quality. For example, a payout is triggered within a 95% confidence interval of a trigger being achieved and a lower payout is triggered if the confidence is only 90% or an even lower payout if the confidence is only 80%. Thus, it can become important for a receiver of payments to ensure that the associated proof increase in confidence to improve payout within such smart contracts. Another approach is to have a payout range and the payouts are triggered within a range of values.

Reselling insurance or bonds as well as premiums within a blockchain or centralized platform. Reselling insurance or bonds could be a syndication where there is a primary insurance or bond holder. The primary bond or insurance holder both invests, evaluates risk and negotiates transaction associated with contracts. The key factor for a decision is risk analysis. This requires a series of validation of issuers and parties involved in the transaction. A second part of the validation is to understand the triggers and the payouts associated with transactions. The primary holder will charge secondary investors (bond or insurance) a small premium or fee for handling the overall transaction and for conducting the relevant risk assessment and developing relevant contracts. The blockchain marketplace can be enabled to conduct the reselling and to manage secondary transactions that take into consideration any fees. At the time of a payout, the chain of investors (secondary or tertiary that could be part of a syndicate) can be automatically managed using the embedded smart contracts with multiple parties within a chain. The rating and/or creditworthiness of the sponsor or issuer is also monitored on a continuous basis and the risks associated with the investment is also monitored. There will be fees associated with these evaluations that can be charged by the platform manager or by the primary investor or jointly thereof within this system. Modeling runs can be managed by third parties to provide forecasting. The associated fees can also be transferred to an investor or an issuer. The method, apparatus or system that is envisioned could handle all such issues or transactions. The platform or exchange can consist of many parts or modules. These modules include 1) Know your customer (KYC) feature (including ratings conducted by third parties, co-parties, or counterparties), analytics of creditworthiness, etc., 2) a transaction or exchange or trading feature, 3) a SPV feature and associated structure, regulations and contracts, 3) a digital watershed or airshed feature (with associated sensors and analytics), 4) a benefits feature (such as a real estate SPV, TIF or other methods of enumerating benefits), 5) a pollutant, treatment and operations and asset management feature including for point- and non-point source, centralized or decentralized, 6) a behavioral gamification feature. All these features can be included in a plug-and-play approach in a modular construct based on a particular need. The KYC feature can be implemented for any or every party (issuers, investors, insurers, etc.) within a transaction, including the description of performance and underlying differential such as velocity (change) or acceleration (second differential change) of performance. An integration can also be conducted over time or space or any other variable to understand performance. The guarantors, insurance and warranties associated with each party can also be explicit. The benefits feature could be integrated, cohosted or separately managed. This feature can be used to understand, record or tabulate improvements to health (and IQ), wealth, income, employment. It could also include features where purposeful development is promoted and incentivized associated with a mitigation or adaptation A treatment/mitigation/adaptation feature could include a centralized or decentralized treatment plant, its performance and upkeep, asset management, and its economy and key metrics. A digital watershed or airshed could include a lake, river, bay, estuary, coast, beach, groundwater system, outdoor air, indoor air, etc. This watershed or airshed is digitized using a monitoring system and its performance is evaluated and prognostics are developed using internal or open source approaches. Investors can hedge for or against an improvement to a watershed or an airshed. The SPV feature can include the participants, employees and the board members of this vehicle, the digital laws, regulations and contracts, and/or all of the automated or manual (voting) features associated with the governance of the overall watershed or airshed. These regulations can for example include procurement features, permit features, specifications, warranties, performance obligations (including for operation or maintenance), etc. A precedence-based approach for example can optionally be used for managing the governance to provide rapid adjudication.

Claims Processing—Claims can be processed on this system using the smart contract approach and through automated banking protocols that can transfer funds when certain conditions are met using optionally an escrow or wallet approach. The method, apparatus or system that is envisioned could handle all such transactions.

The blockchain or centralized platform system is envisioned where a parametric risk or performance warranty can be evaluated and analyzed separately or in combination. As risks are reduced using engineered performance approaches, the rewards of such risk reductions can be shared amongst parties within a transaction thus incentivizing behaviors for risk reduction or meeting performance obligations. For example, a risk of a disaster may carry premiums. Reducing the risk of such disaster by using an engineered approach could reduce such premiums while at the same time introduce a performance warranty of the engineered approach and at the same time bring in new lesser risks. The overall bonding and premium associated with the risk may be lower than the premium associated with the initial risk in the first place. An active system that analyzes, assesses and de-risks existing insurance or financial transactions could work to combine different approaches within a smart contract in an integrative way. For example, a risk of flooding can carry a premium. A levee built to address the flooding could carry a performance warranty associated with the construction and engineering and its operation and maintenance. This levee has a lesser risk of being overtopped or may contain a reverse insurance of premium associated with protection from flooding and a resulting payment for protection. All these risks and warranties (or guarantees) can be optionally brought together in a meaningful way to de-risk an event occurrence and the lowering of overall premiums or resulting savings from de-risking can be shared amongst parties transacting the de-risking. New types of integrated surety or insurance premiums can also be created (using a single insurer or a syndicate) to combine warranties (such as for the wall withstanding a flood) and different types of forward or reverse insurances (for overtopping of the wall and/or for wall being protective) can be bundled in a single surety insurance or a novel and inventive 'Surance Bond' or 'Surance Premium'. The cost of the wall can also be included in a 'whole asset life insurance' approach, where after a single or series of event-based payouts, the asset value is transferred between parties (such as the investor and the issuer or investor and insurer, etc.). Any other example (beyond a flood wall) is also possible that helps mitigated or adapt to acute (such as fire or flood) or chronic (such as pollution) events. Policy incentives can be provided through legislation and regulations to promote de-risking. All of these approaches could be considered within a blockchain, centralized platform or using smart contract approaches. Aggregation of multiple insurance and warranties (as previously mentioned) can also be possible to ensure a system-based end-goal is met by meeting distributed risk or performance obligations. Such aggregation can be developed through its own special purpose vehicle or in a modularized by-law associated within an overall larger multipurpose vehicle. Disaggregation of such risks can also be considered if there are multiple parties and insurers or to address conflict of interest issues.

Dynamic Exchange. A transparent blockchain exchange can be used to buy or sell disaster bonds or other bonds that have conditionalities or warranties for performance (or failure to perform). For example, buy/sell transactions are likely to increase as a disaster approaches, and if a levee for example is used through a resilience bond to mitigate such disasters. Similarly, if property values start increasing as a clean-up progresses or adverse risk is minimized, bond values may change in a blockchain enabled or other forms of exchange. This blockchain (or other types) exchange could have put and call options to manage risk of and for an investor, issuer or insurer. Short selling of a financial instrument, obligation, insurance, warranty, bond, stock or a fund may also be permitted in such an exchange. The advantage of a blockchain (or other types when possible) enabled exchange is the ability to create rapid and immediate transactions typically needed associated with a disaster or 'peak' event for energy, water or other disaster events. The time constants for transactions can change from years, to days, to hours, to minutes, to seconds or less as the event probability changes.

The exchange or transaction can be part of a macrosystem for an entire river basin, an airshed, a watershed, an estuary, where insurance, performance or investments (such as bonds) can be aggregated or distributed (or disaggregated) to achieve overall goals, and/or in a transparent manner. As an example, the assurance of say a water quantity or quality passing through a node or grid within a watershed can be monitored to satisfy the conditions within contracts. Episodic risks such as floods and droughts can be part of an insurance/warranty system within this watershed. The overall exchange assures the engineering performance and participation of a collective within the overall system.

Parties to a transaction: There are typically three parties to a platform such as a blockchain enabled transaction: a sponsor, an investor and/or an issuer. Additional parties could include third party agents and verifiers that are either contracted or self-police or crowd-police the overall platform or blockchain architecture associated with data, modeling, predictions and payouts.

Sponsor: The sponsor is the insurance policy holder or a party (or a SPV/SPA) that needs a project to address a disaster or pollution or a need. Sponsors and/or co-sponsors are responsible for paying premiums or coupons that insure against a disaster or insure for a project performance to mitigate disaster, pollution or non-performance. These sponsors are also direct beneficiaries of any payout. For a performance bond, a sponsor receives conditional payment for non-performance and makes a conditional payment for performance of project funded by any financial instrument, bond, fund or annuity. Sponsors can be individuals, residents, farmers, aggregated groups such as a utility, cities, an industry, or any entity that desires to manage risk or performance. Sponsor also receives a payout if a warranty or performance guarantee is violated.

Investor: Investors come in a variety of shapes and sizes, ranging from individual investors to large pension funds. These investors are typically seeking diversification in their portfolios and are willing to take risk (including the risk of losing their principal invested) for returns on investment. In the case of green or climate bonds, investors (also called impact investors) can also be entities that are seeking to invest in projects that benefit society. In a platform or blockchain driven marketplace, more and different types of investors can be encouraged to participate in the market, especially those that may directly benefit from the investment. For example, the platform or blockchain can support individual investors or regional cooperatives, banking and credit unions that invest in a project within that region to mitigate a hazard or pollution, and therefore benefit from reduced premiums associated with the same hazard, or reduced payments, and fees associated with a pollution discharge. Investors can also be insurance companies that provide or receive a guaranteed future payout for an event or mitigation of an event.

Issuer: There are different types of financial instruments and bonds. Municipal bonds are debt securities issued by states, cities, counties and other governmental entities to fund day-to-day obligations and to finance capital projects such as water and sewer systems. Municipal bonds and similar bonds can also be issued as performance bonds. In this case there is a contingent payment associated with the payment of the bonds to an engineering or contracting entity or concessionaire that invests, builds and/or operates a project for a certain period of time. Issuers can also be an insurance company that issues for example a parametric insurance policy that triggers a payout based on a conditionality. Catastrophe bonds and disaster insurance is an example of a parametric insurance. Other types of insurance are also possible.

An example is a hybrid annuity where the concessionaire may take over existing assets or build new assets or construct new capacity and then operate and maintain them based on a warranty condition being met. Other such example where a performance leads to a payout in a public private partnership model is also envisaged by this invention. The performance of the build and the performance of the operate will be monitored say using a transparent platform or blockchain. For example, embedded sensors can be used to monitor the quality of a concrete pour and the deterioration and life of a concrete or built structure or infrastructure. Other such approaches to monitor the quality of a construction is also possible using satellite imagery, cameras and drones (airborne, marine or submarine). Similarly, the asset operations and maintenance can also be sensorized (outfitted with sensors) using cameras, vibration monitors and water and air quality monitors. The data from any sensing is preferably directly transferred and then management using a transparent and preferably immutable platform or blockchain to bring necessary accountability and improve compliance. Initial capital infusion by the concessionaire will facilitate quick start of projects. Again, in the example case of hybrid annuity, assurance of receiving a reimbursement of say 40% or so of capital cost by completion of the project is an incentive to complete the project on time (the performance of which can be tied to data gathered within the blockchain) whereas linking of remaining operations/maintenance cost to annuities over say between 10-30 years will incentivize the concessionaire for continued performance. Other approaches can involve providing different lifespans for different assets (structural, mechanical and instrumentation) based on longevity and estimated obsolescence rates. The warranties can be broken into parts associated with the estimated life of an asset, thus promoting new approaches to manage assets and its operations based on its own unique lifespan.

ESCO or energy savings contracts can be vehicles within this marketplace or within a performance guarantee approach. Such ESCO can be applicable to industries, utilities, agriculture or individuals that desire to contract out an energy savings guarantee associated with small or large capital changes (costs) that translate into a short- or long-term operational savings. These ESCOs can become part of a blockchain or centralized platform.

Utility rating or scoring systems or management tools and approaches can be considered within a transparent blockchain or centralized platform where sensors, analytics or human voting models can be used to understand utility performance based on criteria and domains such as asset management, engineering, operations, financial health, customer service, sustainability, etc. This transparency is often demanded from public/private utilities (or its customers) and can be provided using such blockchains that can be either public or private. Other platform approaches for transparency are also possible using audits and verification approaches that can blend a mix of privacy and transparency. Pay for performance models can also be brought in. Rating agencies can also score utilities or industries or companies real-time using such approaches. Automated audits can be conducted and some of the audits can be real-time or near real-time.

A Catastrophe (cat) bond is a product to help transfer insurance risk and is an alternative to traditional insurance and reinsurance products. Catastrophe bonds are a way to transfer insurance risks to the capital market and is therefore a hybrid instrument. A special purpose vehicle is used by insurers and reinsurers to issue cat bonds. Cat bonds can pay high interest rates and diversify an investor's portfolio because natural disasters are random occurrences and are not correlated with other economic risk. Depending on the structure of the cat bond, if losses reach a specified threshold, an investor may lose part or all of the principal or interest. Catastrophe bond issuance in 2018 was $9.1 billion and stable after an upward trend and a record high of $10.3 billion in 2017. Cat bond risk capital outstanding in 2018 was $28.7 billion. Most of the risk capital was from US sources. The bond is issued by a sponsor, typically an insurance company. This company identifies a natural catastrophe risk needing coverage. This sponsor also has risk modeling completed to analyze the risk and potential losses. The risk modelers usually employ catastrophe modeling and stochastic risk analysis to estimate the range of potential catastrophes as well as the estimated losses from the hypothetical catastrophe. The sponsor is provided the natural disaster risk coverage into a dollar amount, which becomes the amount of investment the cat bond requires. After risk modelling, the trigger type for the proposed cat bond is established. The trigger type refers to the terms that have to be met in order for the cat bond to be paid out to the sponsor. Triggers for cat bonds are typically indemnity (39%), industry loss (24%), modeled (5%) and parametric index (16%) triggers. After the price and trigger type are decided, the sponsor enters into an agreement with a special purpose vehicle (SPV) and pays premiums for the particular risk coverage. The SPV then packages and sells the bond (alternative risk transfer or ART) through securities to investors. The funds generated through the bond purchase is the collateral that covers the sponsor's risk in case the qualifying event occurs. In return for offering the collateral, the investors receive part of the premiums (from the sponsor for the risk coverage) and the interest from the collateral account. If the qualifying event occurs, this collateral account is liquidated to reimburse the sponsor based on the cat bond agreement and investors will lose the principal.

Parametric insurance. Parametric insurance are payouts that are triggered based on parameters. There could be one, two and/or three or more parameters that could result in a trigger in a single or multiple payout. Parametric insurance therefore is a type of insurance that rather than indemnifying pure loss, ex ante (through forecasts) makes a payment upon a triggered occurrence of an event. The trigger is usually a catastrophic natural event that can result in a loss or a series of losses. Sometimes the loss is much greater and other times the loss is much less than the payout. Instead of basing payments on damage suffered, parametric insurance contracts establish the payout as a function of the occurrence or intensity of event, as determined by a specialized agency such as the U.S. National Hurricane Center. This way, the costs and uncertainty associated with insurance payments are reduced. There is no need to verify and estimate damages, and no potential disagreement or litigation about the payouts. Moreover, the country or the policy holder has immediate access to the resources when the disaster takes place. The first step in building a parametric insurance product is determining the correlation between the index and a drop of revenues or increase of costs for the customers. The insurance can be tiered and have multiple ex-ante considerations (Clarke et al. 2016). Because of the rapid payouts, a record $1.36 billion catastrophe bond was issued by the World Bank last year that relied on parametric triggers to cover earthquake risk in Chile, Colombia, Mexico and Peru (Singer, 2019). The total market for catastrophe bond with parametric triggers since inception through 2017 was $9.67 billion and 16% of overall cat bond market (Hazime, 2017).

Disaster Bonds. Disaster bonds (such as catastrophe bonds) are issued by a special purpose vehicle established by an insurance firm or major investment bank (or both) that structures the terms of the financial transaction, creates the legal framework for implementation, takes responsibility for getting the bond to market, and manages the money held in the collateral account. Such bonds can be part of a blockchain or a blockchain type approach.

Surety Bond. Surety bonds are usually required by contractors and businesses to win contracts by providing the customer with a guarantee that the work will be completed and meets performance requirements. Many public and private contracts require surety bonds, which are offered by surety companies. In terms of revenue, the global surety market was US$15.33 billion in 2018. The demand for surety is a result of increasing demand for restoration of ageing infrastructure of developed economies worldwide. Performance bond is a type of Surety Bond, and value is usually 100 percent of the project size. Surety bonds are issued by a surety and insurance companies that are approved by the U.S. Treasury. Surety bonds are designed to avoid failure of projects and not expected to cover the expected loss in case of failure. Surety bonds manage the project's risks (inherent risk, type of coverage, etc.) as well as the contractor's risks (tangible assets, past performance, etc.) and by charging a risk-adjusted insurance premium. The rates are usually percentage shares of the project value that decrease with project value. For project failure, the surety company guarantees either to finish the project or to abandon the project and pay the surety bond to the agency. Premium in the U.S. varies between 0.5 and 3% of the project value Surance or Surrance Bond or Surance Instrument. We propose as a novel invention, a 'Surance Bond' or a SPV or analogous financial risk management instrument as a combination of 1) either a warranty or a surety bond, 2) a risk mitigation insurance (this is a reverse 'pay for performance' insurance, such as the insurance and resulting premiums for the adequate performance of a flood wall to prevent a flood, and/or 3) risk insurance (such as the risk of flooding). There could be multiple premiums from a single insurer or a syndicate that would package multiple risks into single or multiple premiums with conditionalities based on event triggers associated with defined risks. The premium for a Surance Bond could be between one-third to two-thirds of the premium associated with a disaster risk of a similar magnitude flood or any such event, using a Disaster bond or a parametric insurance or from an indemnity or other insurance. The inventive step is to encourage the building of pollution mitigation or climate change adaptation infrastructure. This bond approach would offer lower premiums and therefore encourage the construction of such infrastructure partly or wholly from the resulting savings from these premiums. The triggers for payout of a Surance Bond or such type of instruments could be similar to a payout for a Parametric Insurance (in the case of pay for performance obligations) and/or indemnity insurance in case of a warranty obligation. The triggers can be unified (all parametric, all modeled or all indemnity) or a combination of parametric, modeled and/or indemnity. It would be preferred that pay out triggers associated with smart contracts should be rapidly estimated and automated, and so these triggers would therefore rely preferably on parametric and modeled approaches for payouts. In the case of a reverse insurance, instead of a modeled loss trigger, it would rely on a modeled loss mitigation/adaptation trigger (modeling the prevention of loss using for example flood walls or green infrastructure). Therefore, a warranty and loss insurance could have modeled loss trigger and the loss mitigation project could have a modeled loss mitigation/adaptation trigger. The same model could be parameterized to simulate the occurrence of a loss or the mitigation of such loss to derive payouts for various scenarios. These scenarios could be developed from a single project (such as a centralized flood wall construction) or from multiple decentralized projects (such as green roofs and water storage in individual houses) to produce different modeled loss or modelled loss mitigation/adaptation scenarios and thus producing large scale collective premium reductions. In such a bond, the warranty value can be as low as one-third or lesser than the full hazard insurance value and the reverse insurance is also as low as one-third or lesser than the full harad insurance value. In any case, the surrance approach should be cheaper than the full hazard insurance value.

Tax increment financing (TIF) is a public financing method that is used as an initial subsidy for development of an infrastructure, and other community-improvement projects in many countries, including the United States. The value generated from the project is captured typically through diverting future property tax revenue increases from a defined area or district toward an economic development project or public improvement project in the community. TIF subsidies are not appropriated directly from a city's budget, but the city incurs loss through foregone future tax revenue. In a blockchain or blockchain type approach, a resident whose taxes are used for a water or energy project that is part of a TIF can evaluate the project performance through a transparent blockchain. The payout for performance can occur automatically and the society overall becomes more directly vested in a project's success.

TIF is a method of allocating revenues to finance infrastructure improvements and economic development efforts within municipalities. A municipality is responsible for choosing where to locate TIF districts within its boundaries. The TIF process splits tax revenue generated from properties within the TIF district into Base revenues and Increment revenue. The base revenue is the amount available before the TIF district (year zero) is established; base revenues are shared among a mix of local governments that have the power to assess property taxes: schools, cities, counties, and special districts. Incremental revenues are new revenues in excess of the base revenues are generated by development projects. These dollars are allocated to the government that sponsors the TIF project. In most TIF districts, the baseline is frozen at the year zero amount; however, in others, the baseline grows at a rate of inflation using a pre-defined methodology. In one example, a TIF was used to build a subway station in New York City. TIF has been criticized when used for residential and commercial development because it merely moves the tax base from one part of the city to another rather than increasing the size of the overall tax base. Thus, TIF is recommended only for logistically complex, or otherwise unprofitable for the private sector to execute projects, such as brownfield improvements and the extension of basic infrastructure like roads, transit, or utilities needed to make further development possible. A TIF-like approach can be used within a SPV or beneficiary SPV where the 'increments' can be collected by the SPV and looped directly into the project as a beneficiary contribution thus improving trust and reducing brokerage or administration costs.

Real Estate Investment Trust, Real Estate Fund and Real Estate trust or SPV. Real estate investment trusts (REITs) allow individuals to invest in income-producing real estate on a large-scale which is difficult for a single investor. A REIT is a company that owns and typically operates income-producing real estate and could be structured as a SPV. These assets could include office buildings, apartments, shopping malls, hotels, resorts and warehouses. REITs are an approach for individual investors to earn income produced through owning commercial real estate without actually having to buy it. There are both exchange and non-exchange traded REITs. Equity REITs own and manage real estate properties. Mortgage REITs hold or trade mortgages and mortgage-backed securities. REITs do not offer much capital appreciation since their structure often requires at least a 90% of income back to investors. Only 10% of taxable income can be reinvested back to purchase new assets in most jurisdictions. They do provide a mechanism for crowd-funding community ownership of local property however, and in some cases could be instrumental in providing environmental change where the stakeholders are the local citizens, provided the regional securities laws allow it.

Real estate funds are investments that allow investors the same benefits of investing in a mutual fund and with similar professional and portfolio management support. Real estate funds can directly invest in assets such as commercial properties, land, apartment complexes, and agricultural space. Real estate funds gain value mostly through appreciation and generally do not provide short-term income to investors the same way that REITs might. The investments for either the REIT or Real estate funds can be made through a trust directly or via Special Purpose Vehicles (SPV). An SPV is a company or a limited liability partnership (LLP) or a public-private partnership in which a REIT holds or proposes to hold an equity stake or interest of say at least 50%. An SPV is not allowed to engage in any activity other than holding and developing a property and any incidental activity. The same could apply to a Real Estate Fund in which case it can be less an income and more a longer-term equity investment. A combination of REIT and Real Estate Fund is also possible to distribute income and equity approaches. Such benefits or increments (associated with income or appreciated investments) can be looped back in part as beneficiary contributions (in the form of cash-flow or equity) to a clean-up or restoration for example in lieu of taxes. If the beneficiary contributions are in the form of equity, this investment could be structured as a fully private, or a cooperative, or a public-private or a fully public investment approach within a development as part of say a land monetization deal. The beneficiary payments or contributions can be tokenized or directly contributed as fiat transfers to the exchange for past, present or future funding of improvements to a watershed or airshed for restoration or resilience. All of the above (TIFs, REITs, real estate funds, betterment levies, etc.) are approaches to promote beneficiary contributions or dues for the energy and environment infrastructure systems invention proposed.

Contingent convertibles (CoCos) are a debt instrument issued by European financial institutions that converts a bond into an equity to help the issuing financial institution absorb a capital loss. Contingent convertibles are similar to traditional convertible bonds. The difference is that a contingent convertible bond is defined with two elements: a trigger and a conversion rate. Similar conversion (based on an event trigger) of equity into a bond or a bond into an equity can be envisioned for a Resilience or a Restoration financing instrument, especially based on risk and uncertainty associated with an improvement or a hazard in both chronic and acute event formats. For example, an increase in uncertainty or increase in risk can trigger conversions from a bond to equity in very much a similar approach. The trigger is a pre-specified event (such as the ratio of a SPV's (or exchange assets) equity to risk-weighted assets falling below a predetermined percentage) causing the conversion process, and the conversion rate is the actual rate at which debt is swapped for equity. The trigger needs to be defined in a way of ensuring automatic and inviolable conversion at different pre-specified event thresholds within a smart contract. The design of the trigger and the conversion rate are critical in the instrument's effectiveness.

Impact Bond: Impact Bond is a special type of Municipal Bond. This bond is structured such that there are contingent payments associated with project outcomes using a pay for success model. This approach allows for the investor and the issuer to share the risk associated with a project. Like other Municipal Bonds, the impact bond consists of an issuer, such as a local government, and an investor and a fixed term. To manage the pay for success scheme, in addition, the impact bond also has additional parties: a financial intermediary that brings in stakeholders and structures the deal, an evaluator that assesses the project outcomes and repayment levels, and a service provider or project implementation partner that services the project or meets the regulatory limit. If the constructed project meets an outcome, a contingent payment is due to the investor. If the project does not meet an outcome, the payment is due to the issuer. This payment can be a fixed amount due at an earlier period usually after the project construction and performance success outcome can be confirmed. Other bond types go much further than the performance of a project and evaluate the restoration of ecosystem based on triggers or else the generation of wealth also from triggers. Alternatively, the reduction of a hazard (increase in resilience) and its benefits can also be converted into cash-flow for bond payouts. These can be triggers in smart contracts that can result in cash flowing to escrows, wallets or collateral accounts.

Speed of transaction: Information can be seen in real-time or near real-time using a blockchain or a hybrid and so transfer of funds can be instantaneous or near instantaneous as well. However, a bank's policy may restrict instant transfer of funds based on value of transfer or the cashflow. An escrow or wallet can be set up to guarantee availability of funds to make the platform or blockchain more relevant. Our expectation is that transaction speeds for data, analysis, modeling and payment with a transparent blockchain can be within minutes and in some cases even within seconds or even less. It is expected that a blockchain type approach may be preferred for an acute event requiring speed of transaction relative to a chronic event that may take years for implementation or benefits to be realized.

An example of three blockchain engines that could be used are Ethereum, Hyperledger Fabric and R3 corda. Any of these three engines can be leveraged to build out a system. Other engines can be used as appropriate in a tokenized or non-tokenized approach. The term token and the term currency (crypto, digital or fiat) are and can be used interchangeably.

Transparency: In the ecosystem there are multiple parties (actors, participants or stakeholders). These could include direct parties and third parties. All of the parties and the history of the parties are transparent in the blockchain system. Each party's characteristics and weightings can be different (number of successful audits for a third party; number of claims processed, or parties insured, for an insurer). Problems and adjudication associated with each party can also be transparently identified within the rating score. Third parties can make up a substantial overhead in a platform or blockchain system. Each party may have a smart contract or smart regulation associated with their being part of the system. The hierarchy of each clause in a smart contract between two parties affecting other parties can be pre-ascertained. These contract or regulation hierarchies can be modeled, and stress tested in advance to ensure robustness and transparency of the platform or blockchain system. The edits to the contract is based on need (and based on concurrence of parties) and its impact on others is also transparent. The credibility of a third party is continuously monitored and ratings (history and quality) can be brought into the platform or blockchain. A decrease in credibility rating or trust rating can automatically trigger a new third party being brought into the platform or blockchain system or the data associated with a third party automatically being deprioritized.

Fraud Management—Multiple claims for a single event can be avoided. The occurrence of a disaster event can be legitimized. False information on performance being met can be verified by modeling or by a cascade of sensors or by using protocols to verify the health of a sensor. Audits can be tracked automatically with warranties associated with such audits all on the blockchain.

Authenticity, Auditability and Traceability: An example is a third-party providing data and information on weather or pollutant. This information can be taken directly from an accredited third-party institution and imported directly into the blockchain system without any human intervention ensuring the authenticity, auditability and traceability of the information. An example is information of a type of hurricane of the nature of a flood. These events have a specific characteristic that results in a trigger. When triggered, by an event, automatic payouts can result increasing trust in the overall process between an investor and a sponsor/beneficiary. Authenticity model example for a flood event may have a certified sensor sending information into a blockchain platform with zero human intervention. Many other disaster events may apply. The blockchain security and characteristics of the technology will prevent any individual from modifying the data. Any mistakes in entry is also recorded in addition to the original data. For example, a trigger may be allowed or disallowed based on the number of times a dataset is modified or intervened. A maximum number of interventions may be allowed in a certain time window. Or if there is an intervention that results in a payout, this intervention can be corroborated using multiple sources either automatically or if needed manually. This decision for automatic or manual corroboration can be recorded within the smart contract. All of these approaches will eliminate fraud.

If there is contradictory information, based on two or three sources, a human voting model can be introduced to validate sources. The time allowed to make a vote can be set in the smart contract to maximize authenticity while at the same time maximize the likelihood of allowing a vote. Algorithms and artificial intelligence (AI) can be used and set to improve the authenticity of a vote (over time and in space) based on multiple parameters including identity, time, location and also typical bias characteristics of a vote or a voter. Evidence associated with a vote can also be collected real-time that can feed into an AI model to manage and eliminate bias.

Automation: Transaction costs from automation and leveraging smart contracts model can be substantially reduced thus overall increasing the number of players as well as lowering the premium values. The triggers can have multiple characteristics (a, b, c and d). A payout can result when a single characteristic is, or multiple characteristics are triggered. Similar approaches can be used for a performance bond. For example, the quality of a wall protecting a flood can be automatically and continuously ascertained using sensors that are placed in a wall or a levee to understand its ability to withstand a flood. If the wall quality deteriorates using a sensor driven or manual audit, triggers are automatically notified. Such notifications can result in changes to premiums associated with insurance or payouts for performance. Penalties can also be automatically triggered if needed to make up for any loss. The smart contracts can also take into account who makes payments based on different triggers. For example, a trigger a and trigger b may result in payments from FEMA and trigger c and trigger d may have payouts occurring from a private insurance player. Other approaches and overlaps of triggers and/or payers (such as insurance companies or financial institutions) and/or payees (beneficiaries including public or private institution and/or individuals) are also possible.

Analytics and Predictive Modeling. Analytics is the analysis of data and developing trends using different learning or non-learning algorithms that may use priors to develop posteriors and also through deep learning mathematical protocols. These analytics are key to improving the efficiency and reduce transaction risk within the blockchain over time. One approach to the analytics is for example to trigger the building of a higher wall or levee to reduce premiums for a beneficiary subject to flooding. Another approach to analytics is the reverse—an increase in premiums associated with a decrease in performance or an increase in likelihood of an event. Thus, one could have fixed, variable or floating premiums or coupons, fixed and variable/floating payouts based on events and performance that are a basis of analytics performed. Overall, such analytics can considerably de-risk the overall transaction through information and transparency thus reducing premiums or coupon payments. The improved efficiency associated with analytics also increases trust. As high ratings are maximized within a blockchain, the overall standards can improve. Predictive modeling helps in the decision-making process, such as through runs can be designed as mock stress tests to mitigate risks, improve efficiency and increase trust in the blockchain system. Analytics can also include data sorting and managing the ratings of key players in the system. These analytics are an important behavioral tool between dispersed transaction parties such as farms and individual homeowners.

Facilitate the netting of payments. Funds can be collected into an escrow or a collateral account and paid out based on some or all of the parameters being triggered. In cases the insurance is insured by multiple companies, the payout amount needs to be collected from these companies using a netting approach. This netting approach can also be made automatic using smart contracts within the blockchain and using escrow/collateral approaches also connected to the blockchain, if needed. The terms escrow, collateral account and wallet can be used interchangeably even though they may have slightly different meanings related to their context (insurance, surety, warranty versus finance, investment, debt obligations).

Proof of work and proof of stake. Both proof of work or proof of stake approaches can be considerations for tokenization or digital currency or for a trade within the platform or exchange. Proof of work approach can be used for example when desiring to allow competition between many parallel adaptation or mitigation approaches. Proof of stake approach can be used for example where significant investment is needed with resulting stakes associated with such investments.

The blockchain can comprise one or more digital storage databases for housing one or more computer models and/or one or more financial instrument transactions. The one or more digital storage databases can be held on a server and/or one or more of said digital storage databases being located on a cloud computing database. The blockchain can be managed by a third-party entity such as a non-profit, a watershed association, an airshed association or an independent scientific governmental or non-governmental body, a supercomputer, or a robot manages the sensors, computing devices or the outputs or also by a development bank or a group that can guarantee, backstop, or ensure payments.

It is understood that the various disclosed embodiments are shown and described above to illustrate different possible features of the disclosure and the varying ways in which these features may be combined. Apart from combining the features of the above embodiments in varying ways, other modifications are also considered to be within the scope of the disclosure. The disclosure is not intended to be limited to the preferred embodiments described above, but rather is intended to be limited only by the claims set out below. Thus, the disclosure encompasses all alternate embodiments that fall literally or equivalently within the scope of these claims.

Some exemplary preferred embodiments of the present disclosure are illustrated in the drawings. FIG. 1 represents an overview of a public or private marketplace where financial instruments in the form of insurance or insurance bonds or its variants, can be bought and sold with corresponding returns or premiums; or payments; where a syndicate of investors or a syndicate of insurers may invest or insure in a performance driven project or a parametric insurance that considers an event risk. The smart contracts can involve infrastructure guarantees and warranties from project execution or conditionalities or contingent payments or mandatory tenders that need to be met for returns on a bond. The arrows in FIG. 1 represent exemplary transactions that are associated with smart contracts that are contained within the overall blockchain or computerized ledger. These contracts are triggered based on manual or automated input that can result in a transaction or a scoring approach. These are exemplary and other embodiments are also possible. The projects are also exemplary and other types of environmental and energy projects are possible. The types of instruments are also exemplary and other embodiments are also possible. The entities can also be other groups than those listed. These transactions or scores can be tokenized as necessary or even converted to a digital currency with a 'proof of work' or 'proof of stake' (associated with water or wastewater treatment, mitigation or adaptation project). So, for example, in lieu of solving a puzzle for a cryptocurrency, the proof of work would be a sensor and analytics driven measurement of a completed task, such as removal of pollutant, or improvement of water quality (i.e. restoration), or reducing risk of a hazard such as floods or other climatic events (i.e. resilience). A digital ledger can tabulate these removals, improvements or risk reductions (both centralized and distributed/decentralized or combination) and to tally the resulting proceeds. Another approach is to provide incentive for such removals, improvements or risk reductions, where those that achieve these changes 'earlier' receive more tokens or digital currency relative to those that do so later. Alternately, the valuation or pricing of such tokens can increase with time as benefits and wealth are accrued (similar to a stock, bond or a mutual fund) This approach could spur much more rapid and creative approaches for attaining restoration or resilience targets ahead of schedule. A harm done conversely will require payments or will reduce valuations. Trading between entities or individuals using such tokens can also be considered where an improvement or performance attained by one entity or individual can be shared or traded with another entity or individual.

An environmental, energy, engineered infrastructure or natural systems exchange platform (stand alone, trust or a SPV) can at least comprise four components: trading engine, a user interface for access to information, a wallet or escrow approach to manage tokens, funds or promissory notes, and a backend administration panel for providing information for the customers.

A trading engine retrieves the orders, or allows for matching of buy/sell orders, or permits the calculation of balances or dues, and/or executes or performs associated transactions based on an event or a confirmation. It is the core of any exchange as without trade engine an exchange cannot function. Ideally, the trading engine and its associated user interface should allow a user to register and access an account, deposit, maintain and withdraw tokens, crypto or fiat currencies, view current order book, past transactions, balances, statistics, view charts and other models and prognostics, place buy and sell orders or investments or insurance or premiums, access the support mechanism is considered as part of the invention.

The user interface and the way traders see the exchange (environmental or energy trading platform and design) from either a computer or a mobile phone is also key to our invention.

The collateral account, escrow or wallet is where the tokens or currency are securely stored with proper encryption approaches. The escrow or wallet can contain two or multiple systems such as a hot and cold walled (with anti-piracy controls) system to diversify and manage risk. The hot wallet permits customers to instantly withdraw coins based on a trigger or need to their external wallet without the need of approval (automated) from an exchange operator, while a cold storage wallet is where the remainder of the coins or tokens are stored with enhanced security. The cold wallet is completely offline even if the hot wallet is hacked.

The administration panel contains and facilitates the use of managing software, business intelligence, analytics, models, prognostics or other advisory or information services and also assists the exchange operator in controlling and managing exchanges. Functions of an admin panel should include altering liquidity, managing exchange software, managing the spread, puts, calls and trading fees, managing user accounts for trading, after verifying KYC or other compliance requirements, managing currencies or tokens crediting fiat deposits, or debiting fiat withdrawals requested by users that include various parties. In addition to these four components that represent the basis of any exchange platform, legal regulation and company or SPA registration should is paramount. Such platforms should also have good security features.

FIG. 1 represents an overview of a public or private marketplace where financial instruments in the form of insurance or insurance bonds or its variants, can be bought and sold with corresponding returns or premiums; or payments; where a syndicate of investors or a syndicate of insurers may invest or insure in a performance driven project or a parametric insurance that considers an event risk. The smart contracts can involve infrastructure guarantees and warranties from project execution or conditionalities or contingent payments or mandatory tenders that need to be met for returns on a bond. The arrows in FIG. 1 represent exemplary transactions that are associated with smart contracts that are contained within the overall blockchain or computerized ledger. These contracts are triggered based on manual or automated input that can result in a transaction or a scoring approach. These are exemplary and other embodiments are also possible. The projects are also exemplary and other types of environmental and energy projects are possible. The types of instruments are also exemplary and other embodiments are also possible. The entities can also be other groups than those listed.

Figure 2:
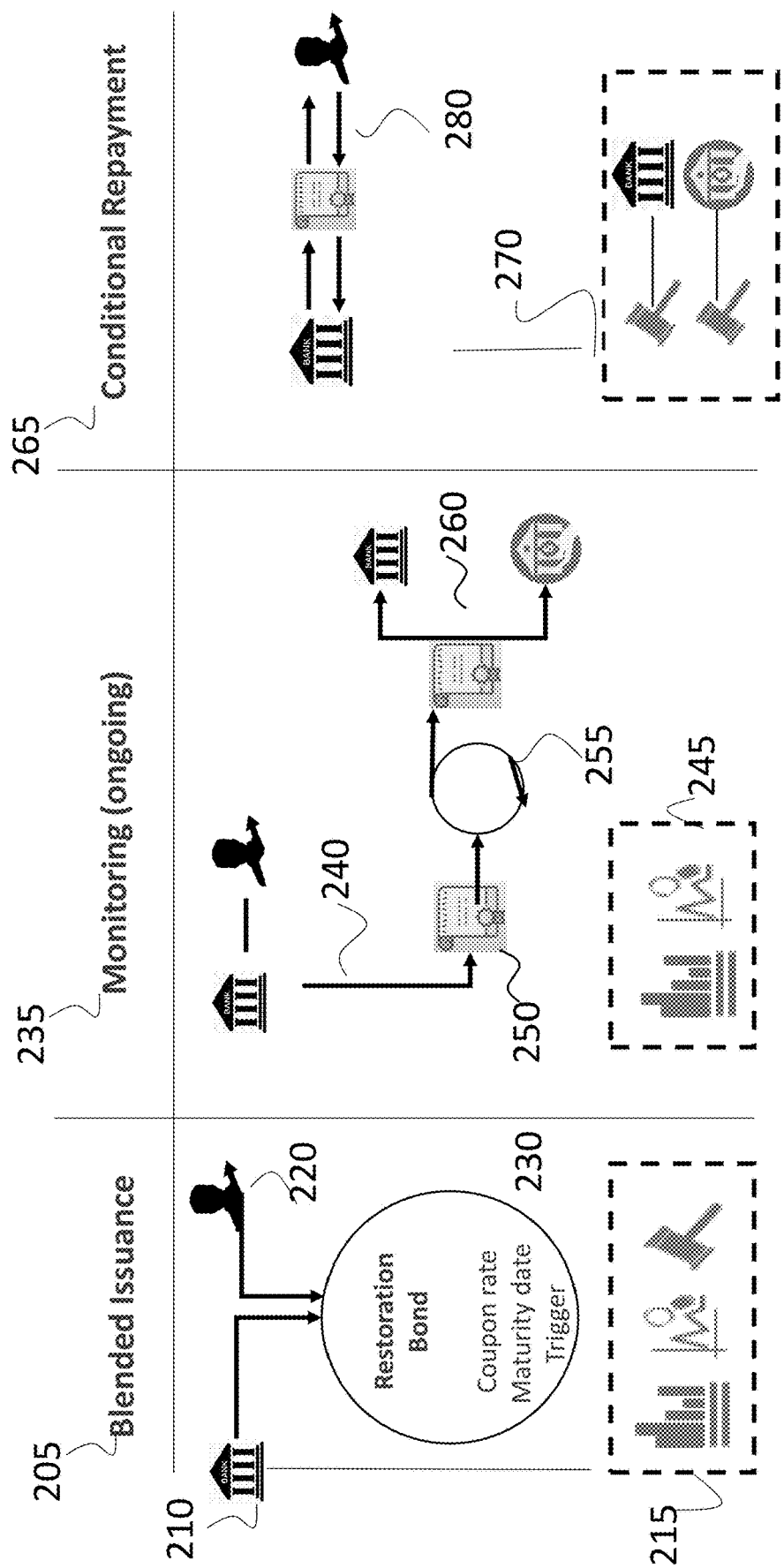
FIG. 2 is an exemplary embodiment of an overview drawing showing a modular approach for implementation of the computerized platform containing digital platforms, although variations may exist where non-tokenized investment options may be used in lieu of tokenized investment.

FIG. 2 is an example implementation of tokenized or non-tokenized platform with smart contract containing triggers and payments. The platform can have multiple types of events including blended issuance 205, monitoring (using sensors and/or analytics) 235 and conditional repayments 265 including the use of smart contracts. These transactions or scores can be a tokenized or non-tokenized menu of investment options 230 (menu of investments transacted within the platform), blockchain or centralized as necessary, or even converted to other digital currency. In a blended issuance approach 205, typically, a bank 210 will issue a bond request for one or more investment options 230, and one or more investors 220 will select the token or non-tokenized investment option including but not limited to a Restoration Bond, Resilience Bond or other bond with differing coupon rates, maturity dates and one or more trigger options 215. In an ongoing monitoring approach 235 typically a bank and one or more investors issue a loan disbursement 240 which is controlled via a smart contract 250 which authorizes completion based on one or more trigger options 245 only if it meets the conditions 255 triggering an alert 260 to a bank and or regulator. In a conditional repayment approach 265 a bank or one or more investors issues a smart contract to the other party 280 which may be another bank, or another group of investors, based on monitoring and discretionary input 270 from a bank or regulatory institution. These approaches could require a 'proof of work' or 'proof of stake' (associated with water or wastewater treatment, mitigation or adaptation project). So, for example, in lieu of solving a puzzle for a cryptocurrency, the proof of work would be a sensor and analytics driven measurement of a completed task, such as removal of pollutant, or improvement of water quality (i.e. restoration), or reducing risk of a hazard such as floods or other climatic events (i.e. resilience) or natural disasters. A digital ledger can tabulate these removals, improvements or risk reductions (both centralized and distributed/decentralized or combination) and to tally the resulting proceeds. Another approach is to provide incentive for such removals, improvements or risk reductions, where those that achieve these changes 'earlier' receive more tokens or digital currency relative to those that do so later. Alternately, the valuation or pricing of such tokens can increase with time as benefits and wealth are accrued (similar to a stock, bond or a mutual fund) This approach could spur much more rapid and creative approaches for attaining restoration or resilience targets ahead of schedule. A harm done conversely will require payments or will reduce valuations. Trading between entities or individuals using such tokens can also be considered where an improvement or performance attained by one entity or individual can be shared or traded with another entity or individual. The repayment that occurs in this figure can occur by converting the tokens into fiat currencies. In a non-tokenized approach, the transaction will always remain in the fiat currencies for heterogenous transaction and project types, with repayments being made for restoration, mitigation or adaptation measures from polluter or treatment fees or from beneficiary contributions. In both cases, the use of smart contracts, sensors and analytics are important features for monitoring and executing transactions. The use of escrows, wallets or collateral accounts can be used to collect such repayments before a smart contract is triggered.

Figure 3:
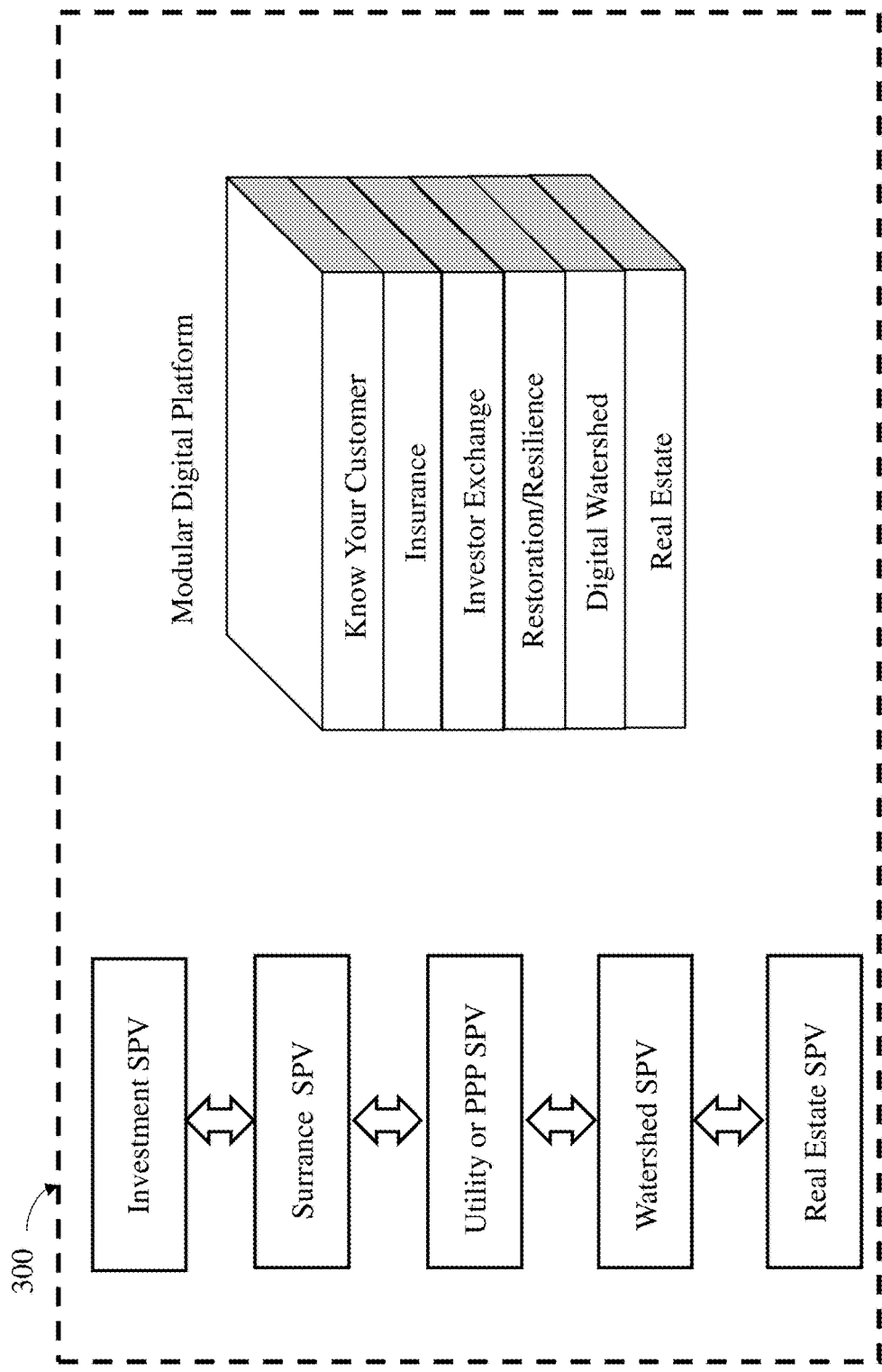
FIG. 3 is an overview drawing showing an exemplary approach of modular governance structures for several independent special purpose vehicles (SPVs) within an overall multipurpose vehicle with each SPV responsible for the associated modules for project finance, operations and maintenance, digital watershed or airshed and associated pollution payment receipts and/or beneficiary contributions such as from improvements to real estate values, while also showing a modular approach for implementation of the computerized platform containing digital platforms. Other approaches such as trusts are also possible and other SPVs can also be modularized.

FIG. 3 describes a project or a watershed restoration or management or an event mitigation (resilience) approach could be part of a special purpose vehicle. The special purpose vehicle (SPV) associated with the adaptation, mitigation or restoration could be unified or linked or connected to other SPVs, such as with a real estate SPV. Thus, an increase in real estate valuations associated with the SPV could then optionally improve valuations of tokens or increase the number of tokens linked to environmental improvements that could have caused such improved valuations. Other linked SPVs are also possible thus directly connecting development (such as tourism improvements, property value increase, health improvements, insurance premium reductions, etc.) to restoration, resilience or environmental improvement. The method, apparatus or system that is envisioned could handle all such issues, events or transactions. These regulations can for example include procurement features, permit features, specifications, warranties, performance obligations (including for operation or maintenance), etc. A precedence-based approach can optionally be used for managing the governance to provide rapid adjudication. A modular platform can also be used containing KYC features, investor or insurance exchange, restoration and resilience infrastructure management, digital watershed, airshed, land, energyshed, soil, and beneficiary and polluter contributions for repayments such as from TIF, tourism, betterment levies, REIT, real estate funds, health care cost savings, and insurance savings.

Figure 4:
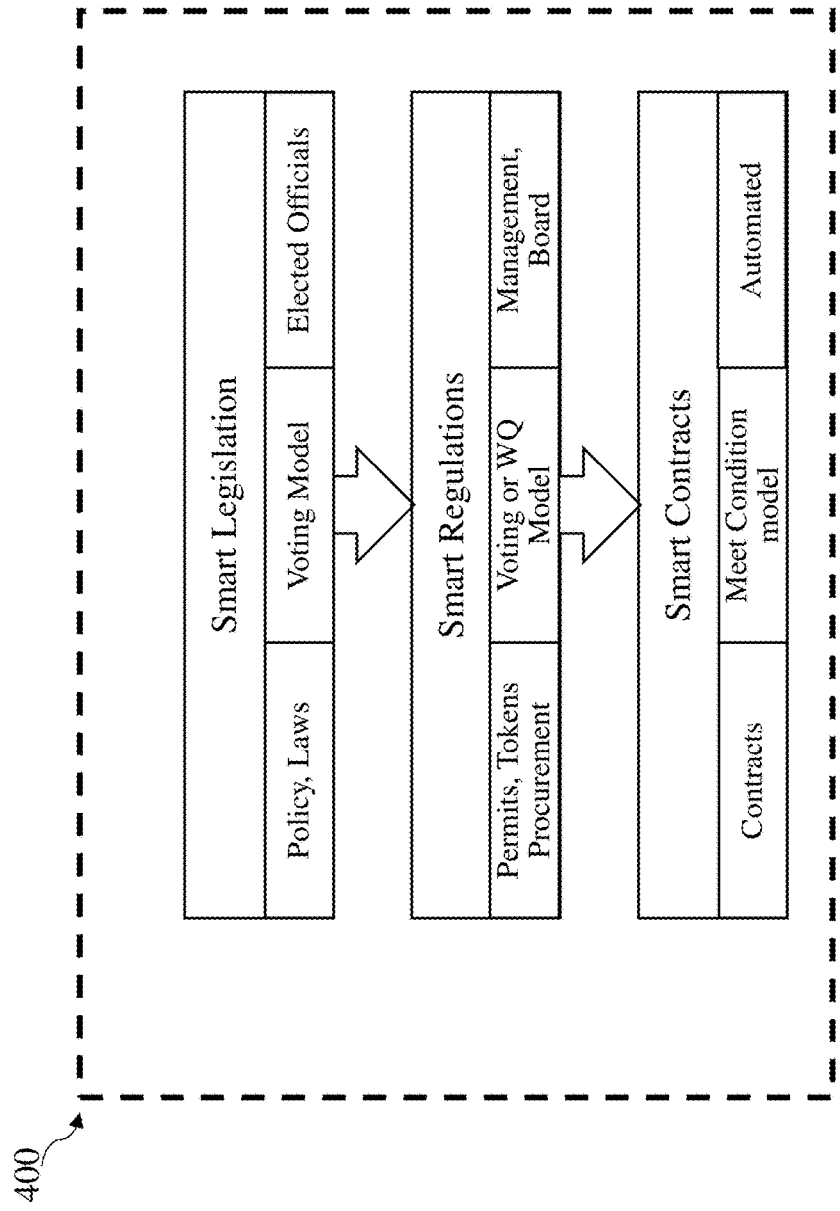
FIG. 4 is an overview drawing showing one exemplary approach for managing such governance of any SPV using smart laws (the ability to develop smart precedence based laws based on say voting models at the council or board level), smart regulations (the ability to add or change such regulations defining the contracts based on crowd sourced triggers and with voting models) and smart contracts (the ability to make payouts based on automated trigger approaches).

FIG. 4 describes one SPV governance approach which can include the participants, employees and the board members of this vehicle executing digital laws, regulations and contracts, and/or all of the automated or manual (voting) features associated with the governance of the overall watershed or airshed.

Figure 5:
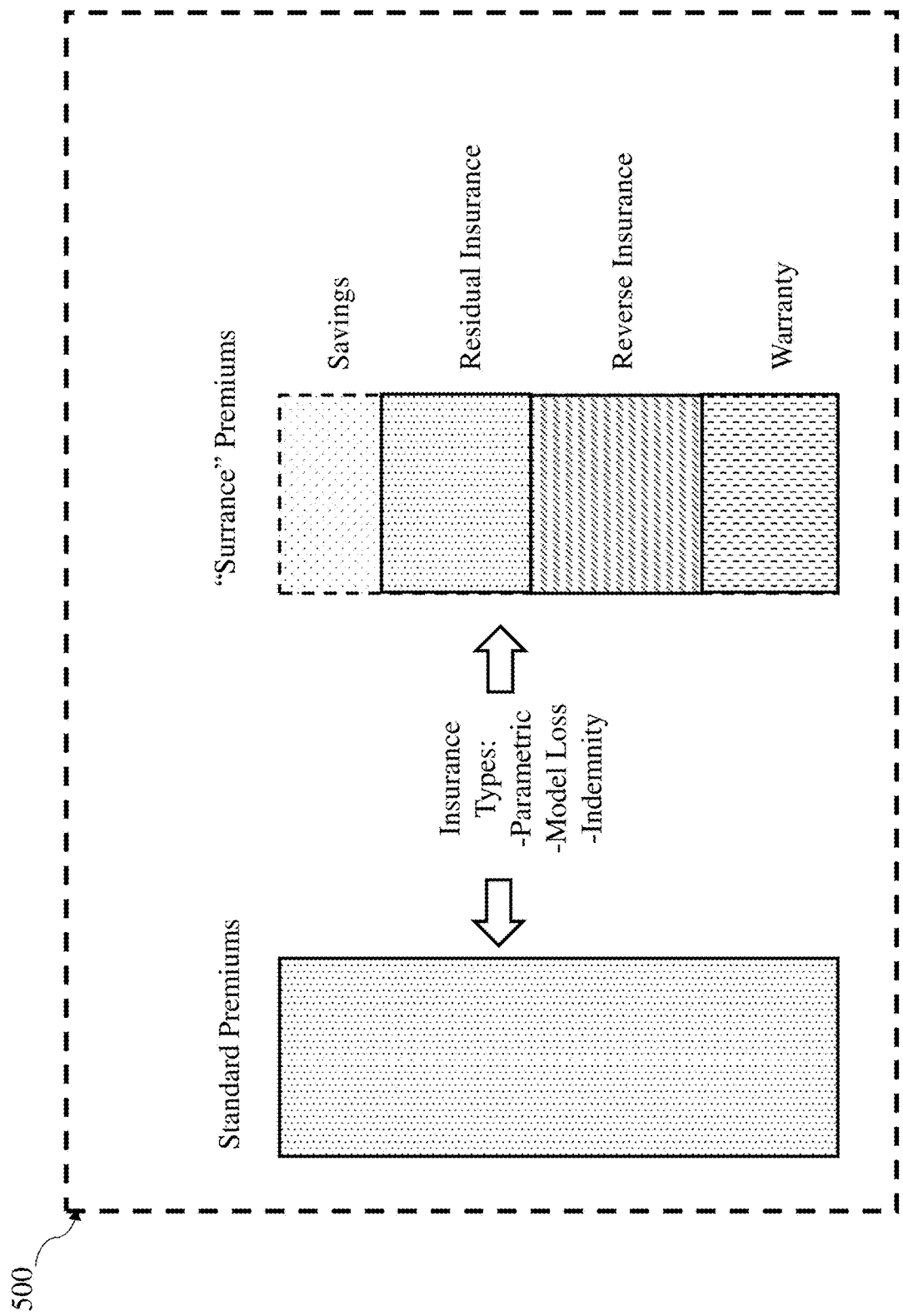
FIG. 5 is an overview drawing depicting exemplary surety approaches for an infrastructure asset class: Standard versus "Surrance" Premiums that combine or bundle warranties, sureties or Surety bonds and insurance (both reverse pay for performance insurance and traditional hazard insurance) that can be structured as indemnity, parametric or modelled approaches.

FIG. 5 describes the new types of integrated surety or insurance premiums that can also be created (using a single insurer or a syndicate) to combine warranties (such as for the wall withstanding a flood) and different types of forward or reverse insurances (for overtopping of the wall and/or for wall being protective) can be bundled in a single surety insurance or a novel and inventive 'Surrance Bond' or 'Surrance Premium'. The cost of the wall can also be included in a 'whole asset life insurance' approach, where after a single or series of event based payouts, the asset value is transferred between parties (such as the investor and the issuer or investor and insurer, etc.). Any other example (beyond a flood wall) is also possible that helps mitigated or adapt to acute (such as fire or flood) or chronic (such as pollution) events. Policy incentives can be provided through legislation and regulations to promote de-risking. All of these approaches could be considered within a blockchain, centralized platform or using smart contract approaches. Aggregation of multiple insurance and warranties (as previously mentioned) can also be possible to ensure a system-based end-goal is met by meeting distributed risk or performance obligations. Such aggregation can be developed through its own special purpose vehicle or in a modularized by-law associated within an overall larger multipurpose vehicle. Disaggregation of such risks can also be considered if there are multiple parties and insurers or to address conflict of interest issues.

FIG. 6 is an example of tokenization based on restoration and resiliency parameters as well as water quality indicators. In this particular example, weights are provided to pollutants or water quality parameters to increase or decrease the relative importance of a pollutant or parameter. Such pollutants or parameters can be tokenized (quantity generated) or alternatively provided valuation (quality improvement or benefits (such as from wealth or tourism)).

Figure 7:
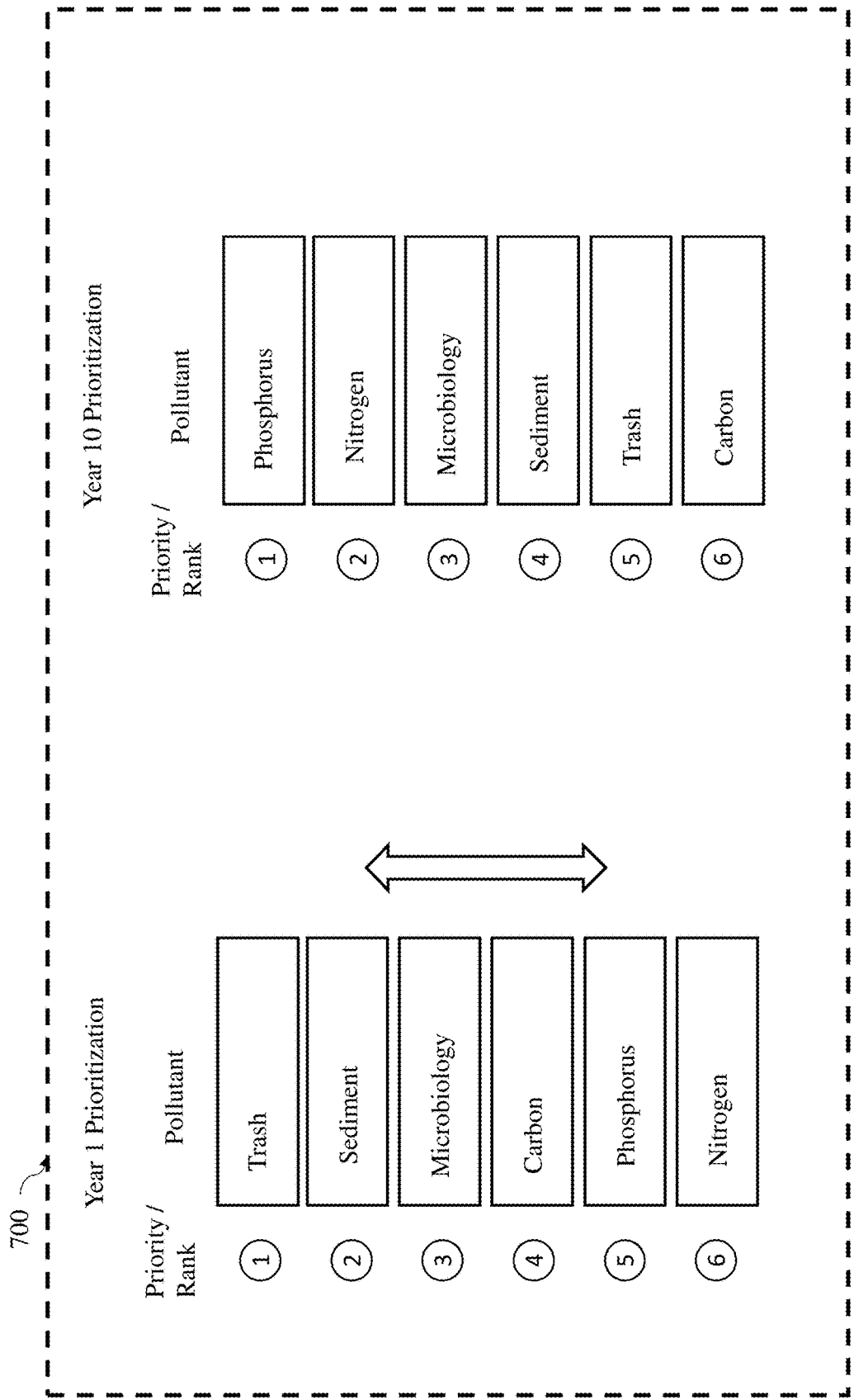
FIG. 7 is an overview drawing showing an example of prioritization of pollutant removal using a weighting approach over time.

FIG. 7 is an example of prioritization of pollutant. Treatment of pollution or the pollutants and the performance of such treatment processes can be subject to conditionalities. The increase in wealth and tax increments associated with industrial activities (that cause pollution) and its clean up can also be subject to future conditionalities. The polluter could be an individual, such as owner of a failed septic tank, or a farmer that uses too much fertilizer or that burns croplands, an industry such as a small tannery or large pharma, or a utility entrusted with managing sewage. The opportunity is for a polluter to become a sponsor or even an investor, where an issuer of a bond or an instrument or a token, develops financial or insurance approaches to any harm caused by pollution and then develops performance conditionalities or warranties for mitigating such pollution. These conditionalities can reduce premiums for pollution or otherwise create incentive conditionalities for addressing pollution. If such desirable performance generates financial benefits for a community (improved health, property values or tourism), such benefits can be looped back in a 'payment for performance' approach. Other pollution prevention approaches are also possible, where 'scarcity' can be engineered with less pollutant being produced in the first place, or conversely 'abundance' can be conceptualized for gradually worsening climatic events. Such scarcity or abundance associated with an event and/or the addressing of such scarcity or abundance can be tokenized. A logging system containing a historian can allow for summing of such events (and associated flow, load or pollution) to allow for triggers and resulting payments to be distributed over an extended time period.

Figure 8:
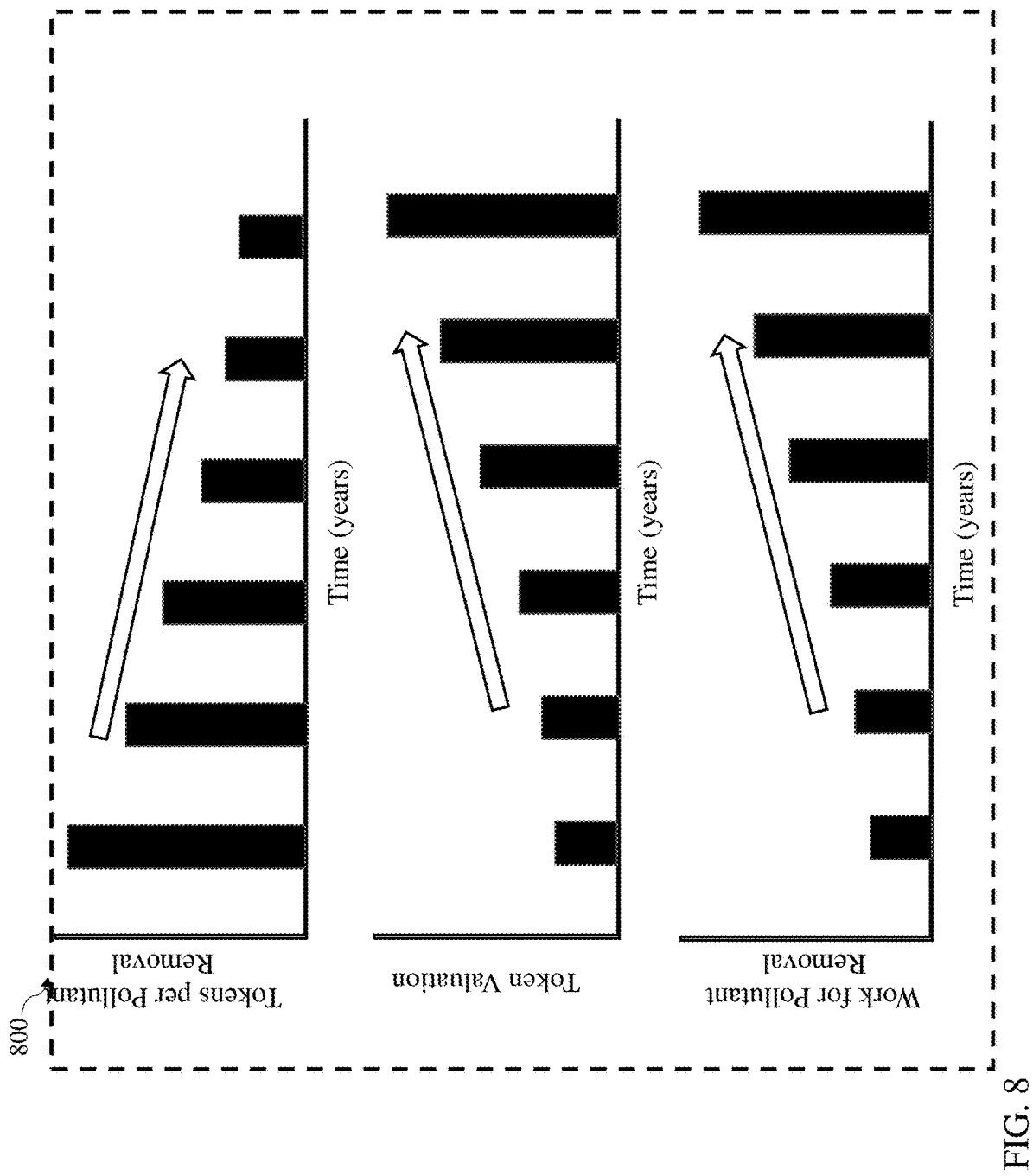
FIG. 8 is an overview drawing displaying an exemplary approach to how the token valuation can be affected by scarcity, beneficiary/polluter contributions accrued, and/or work (operational effort and corresponding cost) to remove pollutant.

FIG. 8 is an overview of how the token valuation can be affected based on scarcity of tokens, beneficiary fee accrued or increase over time, and work (effort) to remove pollutant increasing with time.

Figure 9:
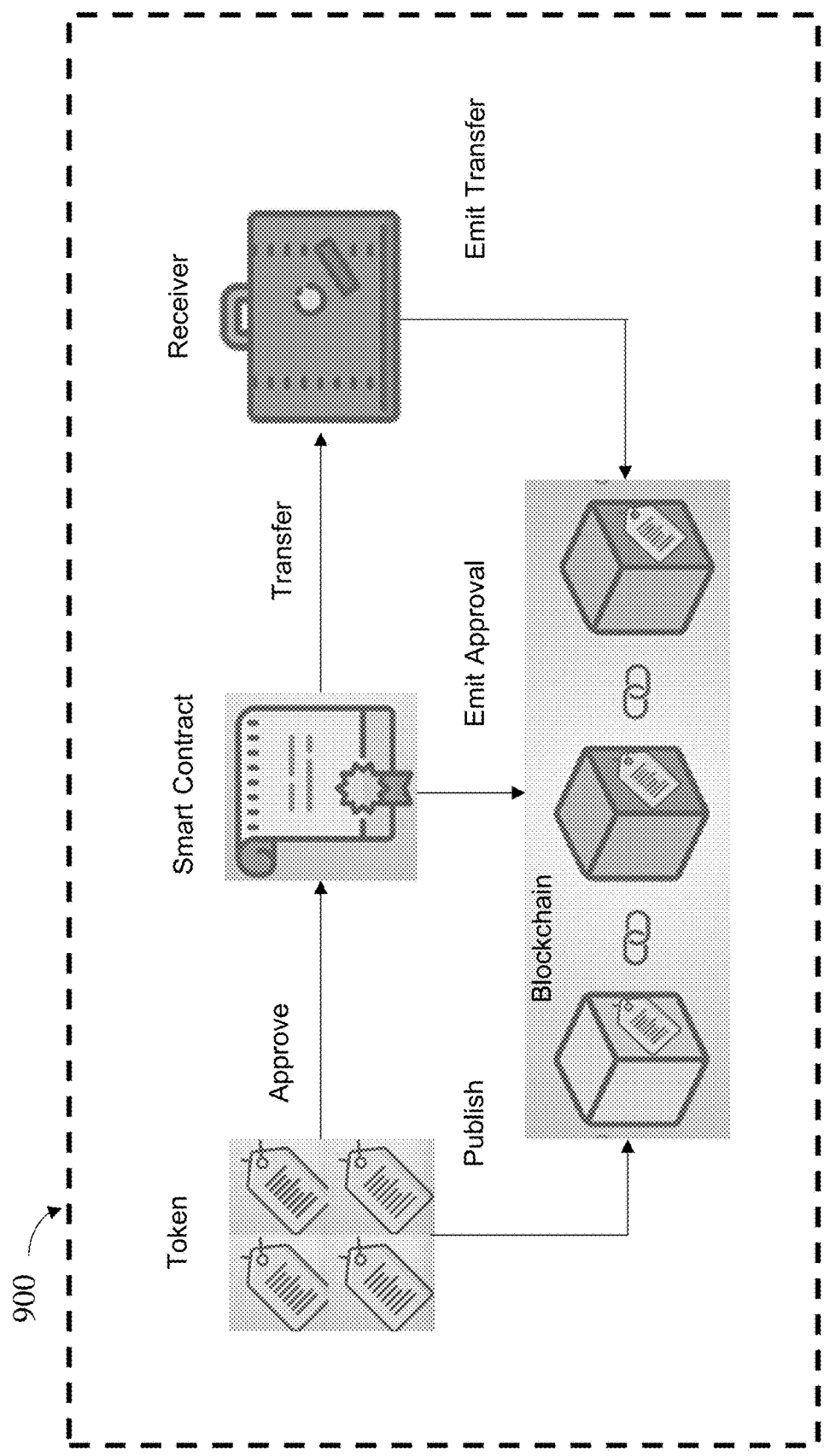
FIG. 9 is an overview drawing illustrating exemplary steps needed to transfer token based on the execution of smart contract within the blockchain framework.

FIG. 9 illustrates the steps needed to transfer token based on the execution of smart contract within the blockchain framework. The tokens are published to the blockchain network. Then the token is assigned a contract address. If that address which holds the token approves a contract to spend on its behalf, the contract then sends the token to a receiver. This is the basis for the token transaction. An example for implementation of tokenization is where tokens are generated for pollutant loads (such as in FIG. 6) or hazards (such as a flood or drought or fire or earthquake) and the mitigation or adaptation of such pollution (such as prevention or treatment or management) or hazard (such as the appropriate infrastructure to address such flood or drought or fire or earthquake) results in a proof of work or proof of stake (the occurrence of such acute or chronic events and of mitigation or adaptation of hazard or pollution) and its monitoring and analytics resulting thereof in an approval and furthermore resulting in a token transfer to a receiver (the party or agent conducting such mitigation or adaptation), the valuation of such token being based on the accrued benefits of such mitigation or adaptation including for example increase in land or real estate value, tourism, health, etc. and/or the valuation of such tokens being based on assessed hazard fees (such as impervious surface area charge associated with storms or floods or excess water consumption fees associated with drought or such fees associated with increasing fire or earthquake risk) or pollution discharge fees (including stormwater or wastewater fees).

Figure 10:
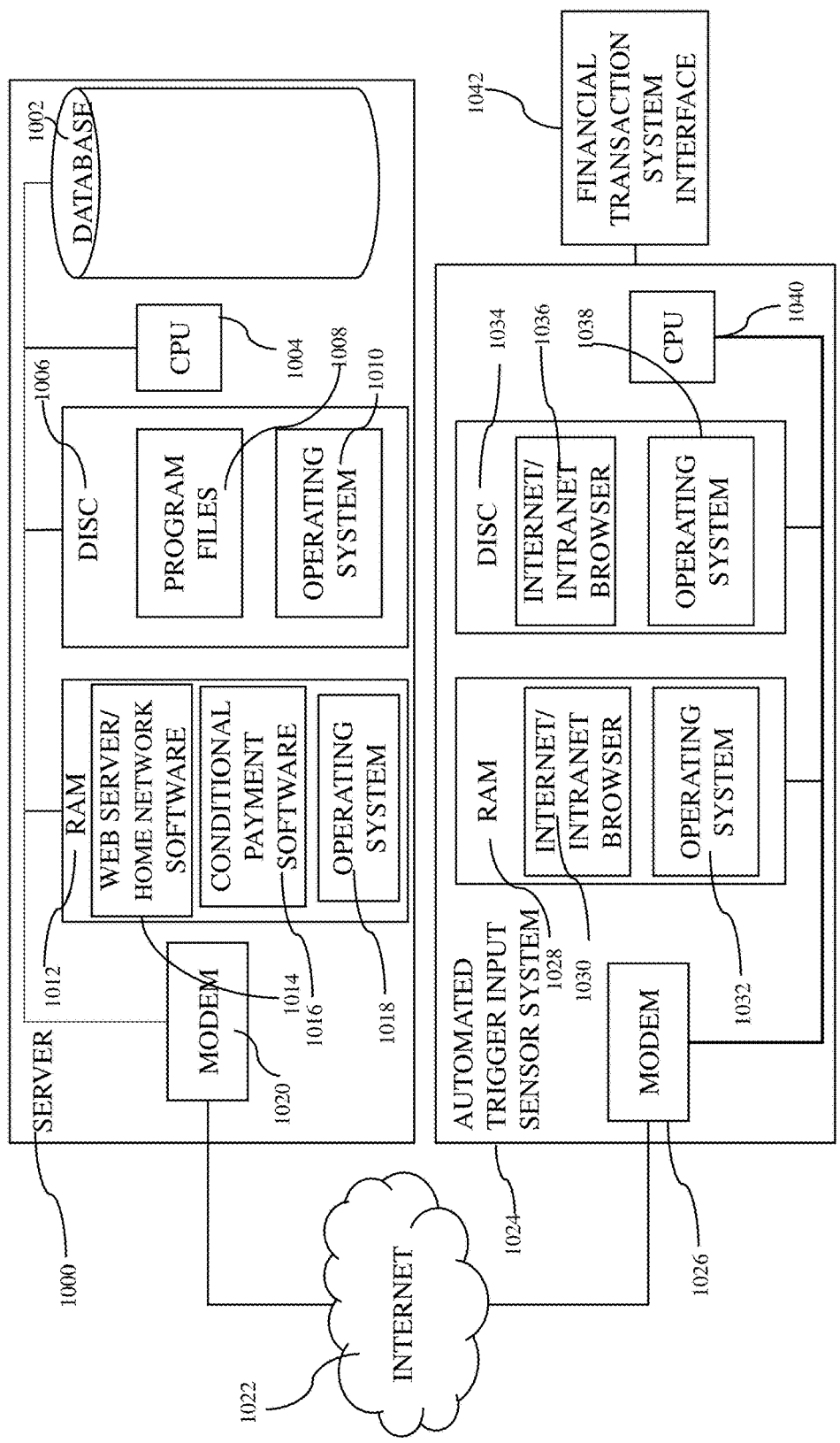
FIG. 10 is an exemplary flowchart showing the typical database hierarchy with data sent to and from a device including but not limited to an automated system of trigger input sensors or analyzers using an application which may process a variety of functions to manage financial transactions accordingly.

FIG. 10 is an exemplary flowchart showing the typical database hierarchy following a standard Internet architecture in which an automated trigger input sensor system 1024 and a server 1000 are connected via the internet 1022 and modems 1026, 1020 or other communications channels. The server 1000 is accessed via the automated trigger input sensor system 1024 operating an internet/intranet browser 1030 or other software application residing in RAM memory 1028 that allows it to display information downloaded from a server 1000. The server system 1000 runs server software 1014, including the Conditional Payment Software 1016 of the present disclosure, which interacts with the automated trigger input sensor system 1024 and a financing database 1002. The database 1002 contains payout information established by system users. The conditional payment software 1016 in some situations will notify any number of users of updates made to the database 1002. Both the server 1000 and the automated trigger input sensor system 1024 include respective storage devices, such as hard disks 1006 and 1034 and operate under the control of operating systems 1018, 1032 executed in RAM 1012, 1028 by the CPUs 1004, 1040. The server storage device 1006 stores program files 1008 and the operating system 1010. Similarly, the user storage devices 1034 store the internet/intranet browser software 1036 and the operating systems 1038. Typically, the financial transaction system interface 1042 would be accessed by users via a computing device utilizing the automated trigger input sensor system 1024. Here data is sent to and from a device including but not limited to a system of trigger detecting sensors or event detecting sensors using an application which may process a variety of functions including but not limited sensing when one or more preset triggers for restoration thresholds or event levels are met and sending data regarding said triggers or events to one or more devices or databases where that information may be stored and a decision made, including a decision to pay, not pay or adjust a payment accordingly to one or more users.

This invention has repeatedly discussed beneficiary payments. The novelty and inventiveness of these payments are critical to the environment sector to meet the sustainable development goals for access to clean air and clean water and low cost energy. The polluter or hazard payments are simply not enough in most cases to deliver a project. Our goal is to have such beneficiary payments to comprise at least 20% and preferably as much as half or more of the overall payments for a energy, environment and natural disaster solution or project.

The present disclosure seeks to further the art by informing those of ordinary skill on how to overcome those barriers. Exemplary embodiments of the present disclosure concern a type of water or energy financing blockchain system called an 'eco-blockchain' system, which is a blockchain insurance claims processing or settlement system and/or a bond, stock, fund, annuity, hybrid annuity, fund or other financial transaction system. In some exemplary embodiments of the present disclosure an eco-blockchain system comprises one or more: sponsors, issuers, insurers, and stakeholders, where the stakeholders are farmers, residents, dischargers, individuals, governmental and non-governmental agencies, businesses, regulators or other third parties. The envisioned embodiments of the disclosure include but are not limited to the following:

1. An insurance or warranty or performance claims processing, settlement system, or special purpose vehicle, special purpose vehicles, or a financial transaction system including financial investments, bonds, stocks, funds, annuities, hybrid annuities that can be modularized comprising one or more sensors and two or more of the following: one or more sponsors, one or more insurers, one or more investors, one or more issuers, one or more builders, one or more contractors, farmers, residents, dischargers, individuals, governmental and non-governmental agencies, businesses, regulators or other third parties, wherein:
    a. an environment or energy or infrastructure or natural systems or related insurance and/or performance guarantee or warranty and/or conditional and/or contingent payment are transacted
    and
    b. premiums, warranties, performance guarantees, coupons, tokens or payouts are transacted between any two or more of sponsor or sponsors, insurer or insurers, investor or investors, builder or builders, contractor or contractors, single or multiple farmers, residents, dischargers, individuals, governmental and non-governmental agencies, businesses, regulators, based on single or multiple performance or warranty condition or within a pre-defined hierarchy of conditions, or using parameters, or events, whole or in part,
    and
    c. said claim condition or conditions and/or performance or warranty condition or conditions or parameters or events are triggered by data or analysis, resulting in a payment or repayment using funds, fees, levies, interest, equities or tokens from polluters or beneficiaries
    or
    d. a shared database is transparent to all the stakeholders,
    or
    e. a smart contract or contracts are used to automatically process said claim condition or conditions and/or said performance or warranty condition or conditions and/or parameter or parameters, or events,
    or
    f. an escrow, wallet or collateral account that is used for netting of payment, or
    g. a know your customer rating interface assists with such transaction,
    or
    h. every transaction and changes are permanently recorded in an immutable database,
    or
    i. the message protocol is baked into the database for real-time processing and visualization.
2. A blockchain marketplace or exchange system comprising at least two or more groups of the following: a sponsor or sponsors, an insurer or a syndicate of insurers, an investor or a syndicate of investors, an issuer or issuers, or builder or builders, contractor or contractors, farmers, residents, dischargers, individuals, governmental and non-governmental agencies, businesses, regulators or other third parties other third parties, wherein:
    a. an environment or energy related warranty, performance or insurance is transacted, and/or related financial investment bond, stock, annuity, hybrid annuity, fund or other financial instrument is transacted directly or within a trust or trusts or special purpose vehicle or vehicles in a modular approach as desired,
    and
    b. a sponsor or sponsors establishes an insurance need or request and issuers or multiple issuers underwriting or compete to underwrite this need or request that contains conditions, and/or a sponsor or sponsors establishes a need or requirement to build an environment or energy project or associated built or natural infrastructure that contains conditions,
    and
    c. insurer, reinsurers, or multiple insurers, or multiple reinsurers can invest or divest the insurance in a single, multiple or a series of transactions, and/or where investors, builders, contractors, businesses or individuals can invest or divest in the said project or infrastructure in a single, multiple or a series of transactions, and
d. beneficiaries make payments or repayments in the form of premiums, coupons, or otherwise directly using funds derived from special purpose vehicles or trusts, or from fees, levies, interest, income, equities
or
e. a shared database is transparent to all the stakeholders,
or
f. a smart contract or contracts are used to automatically process said transaction, investments, coupons or premiums to investor or syndicate of investors, and/or to insurer or syndicate of insurers, and/or to builders or contractors or businesses or individuals through crowdsourcing or other means,
or
g. every transaction and changes are permanently recorded in an immutable database,
or
h. the message protocol is baked into the database for real-time processing and visualization.

3. A system of claim 1 wherein said:
   a. environment is water quantity, quality or any associated infrastructure; air quantity or quality or any associated infrastructure; soil quality, mudslides, earthquakes or fire or any associated infrastructure;
   or
   b. energy could be any part of a grid infrastructure or energy generation infrastructure including but not limited to solar, wind, hydroelectric, nuclear, natural gas or coal.

4. A system of claim 1 wherein said transactions include:
   a. performance guarantees, contingent and conditional instruments,
   or
   b. sureties and insurances including warranties, surety bonds, disaster bonds, catastrophe bonds, parametric insurance, indemnity insurance, modeled or modeled loss insurance, resilience bonds,
   or
   c. contingent convertible financial instruments, bonds, stocks, equity or debt instruments, restoration bonds,
   or
   d. beneficial repayments including tax increment financing, betterment levies, real estate funds or trusts or SPVs, travel or tourism fees or dues, mortgage bonds, restoration bonds, performance bonds, hybrid annuity or bank guarantees,
   or
   e. polluter fees and payments including municipal or industrial discharge fees, stormwater fees.

5. A system of claim 1 wherein said data is in the form of text, numbers, single media or multimedia, alphanumeric, photos or videos and sensing can be audio, visual, vibration, touch or through the detection of chemical or heat signatures from an:
   a. airshed,
   b. watershed,
   c. land or soil,
   or
   d. energyshed.

6. A system of claim 1 wherein the warranty can be for
   a. a project or grey or green infrastructure asset types,
   or
   b. flood or drought management infrastucture including reservoirs, groundwater, levees, dams or wall construction performance and levee, dams or wall operation and maintenance performance,
   or
   c. pollution management infrastructure including a treatment plant construction performance, a treatment plant operation performance, a dam performance, a fire protection performance or earthquake protection infrastructure performance
   or
   d. the performance of an energy grid or performance of an energy generation project.

7. The system of claim 1, wherein a watershed or airshed or soil environment improvement or hazard reduction performance goal is being met.

8. The system of claim 1, wherein the performance or risk can be distributed in a grid or in nodes in a manner that such risks or performance can be weighted, aggregated, prioritized, valued, and/or tokenized.

9. The system of claim 2, where an insurance risk associated with a hazard can be de-risked and/or transacted in an instrument such as a bond which result in protection, savings or payouts to sponsor or sponsors using a combination of
   a. a warranty or surety associated with a built adaptation or mitigation infrastructure cost is less than one-third to half of full hazard insurance value,
   and
   an additional insurance instrument or combination of insurance instruments including a reverse pay for performance insurance or a residual hazard insurance wherein the reverse insurance value is less than one-third to half of full hazard insurance value 10. The system of claim 1, wherein a insurance risk can be adjusted and/or transacted using a warranty instrument or instruments and resulting savings or increases in payments are made as a result of such assessments.

11. The system of claim 1, wherein one or more of said sensors are fixed, or mounted, on a satellite or in a drone or a buoy or a water vehicle.

12. A system of claim 2 wherein:
    a. the environment is any one of water quantity or quality or associated infrastructure; air quantity or quality or associated infrastructure; soil quality, mudslides, earthquakes or fire or associated infrastructure;
    or
    b. the energy is any one or any part of a grid infrastructure or energy generation infrastructure including but not limited to solar, wind, hydroelectric, nuclear, natural gas or coal.

13. A system of claim 2 wherein said transactions include:
    a. performance guarantees, contingent and conditional instruments
    b. sureties and insurances including warranties, surety bonds, disaster bonds, catastrophe bonds, parametric insurance, indemnity insurance, modeled or modeled loss insurance, resilience bonds,
    c. contingent convertible financial instruments, bonds, stocks, equity or debt instruments, restoration bonds,
    d. beneficial repayments including tax increment financing, betterment levies, real estate funds or trusts or special purpose vehicles, travel or tourism fees or dues, mortgage bonds, restoration bonds, performance bonds, hybrid annuity or bank guarantees or insurance savings, or e. polluter fees and payments including municipal or industrial discharge fees, stormwater fees.

14. A system of claim 2 wherein said data is in the form of text, numbers, single media or multimedia, alphanumeric, photos or videos and sensing can be audio, visual, vibration, touch or through the detection of chemical or heat signatures.

15. A system of claim 2 wherein said warranty is for:

a. a project or grey or green infrastructure asset types, b. flood or drought management infrastucture including reservoirs, groundwater, levees, dams or wall construction performance and levee, dams or wall operation and maintenance performance, c. pollution management infrastructure including a treatment plant construction performance, a treatment plant operation performance, a dam performance, a fire protection performance or earthquake protection infrastructure performance, or d. the performance of an energy grid or performance of an energy generation project.

16. The system of claim 2, wherein a watershed, airshed or land, soil environment goal is being met.

17. The apparatus of claim 2, further comprising one or more sensors used to detect the occurrence of said real world events and transmit data regarding said occurrences to one or more said computing devices.

18. The system of claim 17, wherein one or more of said sensors are fixed, or mounted, on a satellite or in a drone or a buoy or a water vehicle.

19. The system of claim 1, wherein the performance of a system can be as large as a river basin or a large watershed, airshed or soil system that can be broken up and/or distributed into smaller scale performance or warranty obligations.

20. A blockchain marketplace exchange system for financing a mitigation or adaptation using green, grey or built infrastructure associated with a natural or environment system including an airshed or a watershed or a natural disaster, that comprises one or more of the following:

a. tokenized smart contracts upon conditional accomplishment of such mitigation or adaptation, and the value or quantity of token or tokens that are approved or transferred increases or decreases: based on the relative or absolute hazard or pollution and the corresponding accrued benefits associated with mitigation of such hazard or pollution, or based on a prioritization or weighting of such hazard or pollution or its adaptation or mitigation, including transferring tokens to such receiver for having conducted such adaptation or mitigation, and the receiver thereby trading such tokens or otherwise receiving b. associated beneficiary payments accrued from decrease in insurance costs, decrease in such hazard or pollution, or incentives, fees, taxes, levies or direct fiat transfers from increase in value of land, real estate, tourism or health, or c. associated hazard or polluter payments including associated fees or levies associated with increasing or causing such hazard or pollution.

The invention is not limited to the structures, methods and instrumentalities described above and shown in the drawings. The invention is defined by the claims set forth below. What is claimed and desired to be protected by Letters Patent of the United States is:

The invention claimed is:

1. A system comprising:

one or more sensors, and one or more engineered infrastructure or infrastructures in a watershed or airshed that is subject to real world events consisting of a pollutant load or a hazard, the one or more sensors measuring the pollutant load or hazard in one or more of engineered infrastructure, infrastructures, or the environment of the watershed or airshed, wherein the engineered infrastructure reduces the risk of the pollutant load or hazard in the environment of the watershed or airshed; and one or more computing devices that contains storage devices, random access memory (RAM), and computer processing unit (CPU), the one or more computing devices configured to receive data regarding the reduction of risk, including mitigation or adaptation with one or more engineered infrastructure or infrastructures of the measured pollutant load or hazard within the watershed or airshed from the one or more sensors; determine using a mathematical model or from analysis, a prediction of performance of the one or more engineered infrastructure, with the prediction of performance resulting in one or more triggers that incentivizes the performance of the one or more engineered infrastructure or a payout between two parties, evaluate whether or not one or more present triggers for the risk or the reduction of risk, of the pollutant load or hazard in the environment of the watershed or airshed, has been met within a specific timeframe or upon the occurrence of a detected event based on the data from one or more sensors measuring the pollutant load or hazard regarding mitigation or adaptation of the measured pollutant load or hazard within the watershed or airshed from the one or more sensors in comparison with the mathematical model or analytical prediction of performance;

based on a determination that the one or more preset triggers, set using the mathematical model or analytical prediction of performance, has been met or not met based on this comparison, generate a token or tokens within a blockchain; and provide a valuation of the generated token or tokens based on the data regarding mitigation or adaptation of the measured pollutant load or hazard within the watershed or airshed from the one or more sensors with the prediction, the valuation of such token or tokens incentivizing a payout between two or more parties, or incentivizing the improvement in performance of the engineered infrastructure.

2. The system of claim 1, wherein one or more of said sensors are fixed, or mounted, on a satellite or in a drone or a buoy or a water vehicle.

3. The system according to claim 1, wherein whether or not one or more present triggers has been met is evaluated based on the data regarding mitigation or adaptation of the measured pollutant load or hazard within the watershed or airshed from the one or more sensors and a modeled loss mitigation or adaptation analysis, and the valuation of the generated token or tokens is provided based on the data regarding mitigation or adaptation of the measured pollutant load or hazard within the watershed or airshed from the one or more sensors and the modeled loss mitigation or adaptation analysis.

4. A method comprising:
measuring a pollutant load or hazard in an engineered infrastructure or infrastructures and the environment of the watershed or airshed by one or more sensors, in a watershed or airshed that is subject to real world events consisting of a pollutant load or a hazard;
receiving, by one or more computing devices that contains storage devices, random Access memory (RAM), and computer processing unit (CPU), data regarding the reduction of risk, including mitigation or adaptation of the measured pollutant load or hazard within the watershed or airshed from the one or more sensors;
evaluating, by the one or more computing devices, whether or not one or more present triggers, set using a mathematical model or analytical prediction of performance of the engineered infrastructure or infrastructures, has been met based on comparing the data regarding mitigation or adaptation of the measured pollutant load or hazard within the watershed or airshed from the one or more sensors with the preset trigger; wherein based on a determination whether-the one or more preset triggers has been met or not met within a specific timeframe or upon the occurrence of a detected event, the system further generates a token or tokens within a blockchain; and
provides a valuation of the generated token or tokens, by the one or more computing devices, based on the data regarding mitigation or adaptation of the measured pollutant load or hazard within the watershed or airshed from the one or more sensors, the valuation of such token or tokens incentivizing a payout between two or more parties, or incentivizing the improvement in performance of the engineered infrastructure.

5. A method, comprising:
measuring a pollutant load or hazard in an engineered infrastructure or infrastructures and the environment of the watershed or airshed by one or more sensors, in a watershed or airshed that is subject to real world events consisting of a pollutant load or a hazard;
receiving, by one or more computing devices that contains storage devices, random access memory (RAM), and computer processing unit (CPU), data regarding the reduction of risk, including mitigation or adaptation of the measured pollutant load or hazard within the watershed or airshed from the one or more sensors;
evaluating, by the one or more computing devices, whether or not one or more present triggers, set using a mathematical model or analytical prediction of performance of the engineered infrastructure or infrastructures, has been met based on comparing the data regarding mitigation or adaptation of the measured pollutant load or hazard within the watershed or airshed from the one or more sensors with the preset trigger; wherein whether or not one or more present triggers has been met is evaluated based on the data regarding mitigation or adaptation of the measured pollutant load or hazard within the watershed or airshed from the one or more sensors and a modeled loss mitigation or adaptation analysis, and the tokens or digital currency are provided as payout based on the data regarding mitigation or adaptation of the measured pollutant load or hazard within the watershed or airshed from the one or more sensors and the modeled loss mitigation or adaptation analysis.

6. A system comprising:
one or more sensors, and one or more engineered infrastructure or infrastructures in a watershed or airshed that is subject to real world events consisting of a pollutant load or a hazard, the one or more sensors measuring the pollutant load or hazard in one or more of engineered infrastructure or infrastructures or the environment of the watershed or airshed, wherein the engineered infrastructure reduces the risk of the pollutant load or hazard in the environment of the watershed or airshed utilizing a digital ledger to tabulate improvements, removals or risk reductions in a decentralized manner; and
one or more computing devices that contains storage devices, random access memory (RAM), and computer processing unit (CPU), the one or more computing devices configured to
receive data regarding the reduction of risk, including mitigation or adaptation with one or more engineered infrastructure or infrastructures of the measured pollutant load or hazard within the watershed or airshed from the one or more sensors; determine using a mathematical model or from analysis, a prediction of performance of the one or more engineered infrastructure, with the prediction of performance resulting in one or more triggers that incentivizes the performance of the one or more engineered infrastructure or a payout between two parties,
evaluate whether or not one or more present triggers for the risk or the reduction of risk, of the pollutant load or hazard in the environment of the watershed or airshed, has been met within a specific timeframe or upon the occurrence of a detected event based on the data from one or more sensors measuring the pollutant load or hazard regarding mitigation or adaptation of the measured pollutant load or hazard within the watershed or airshed from the one or more sensors in comparison with the mathematical model or analytical prediction of performance; , wherein based on a determination whether-the one or more preset triggers has been met or not met within a specific timeframe or upon the occurrence of a detected event, the system further generates a token or tokens within a digital ledger; and
provides a valuation of the generated token or tokens, by the one or more computing devices, based on the data regarding mitigation or adaptation of the measured pollutant load or hazard within the watershed or airshed from the one or more sensors, the valuation of such token or tokens incentivizing a payout between two or more parties, or incentivizing the improvement in performance of the engineered infrastructure.

7. A system of claim 6 wherein the token or valuation of the token is a digital currency.

8. A system according to claim 6 wherein a hazard results in a loss or damage, or an improvement associated with a hazard mitigates a loss or damage or adapts to prevent or reduce a loss or damage.

* * * * *